US010188302B2

(12) United States Patent
Ziedins et al.

(10) Patent No.: US 10,188,302 B2
(45) Date of Patent: Jan. 29, 2019

(54) METHODS FOR DYNAMIC VISUALIZATION OF CLINICAL PARAMETERS OVER TIME

(71) Applicant: The University of Vermont and State Agriculture College, Burlington, VT (US)

(72) Inventors: Kathleen B. Ziedins, Waterbury Center, VT (US); Christopher M. Danforth, Burlington, VT (US); Thomas Orfeo, Colchester, VT (US); Stephen J. Everse, South Burlington, VT (US); Kenneth G. Mann, Colchester, VT (US)

(73) Assignee: The University of Vermont and State Agriculture College, Burlington, VT (US)

( * ) Notice: Subject to any disclaimer, the term of this patent is extended or adjusted under 35 U.S.C. 154(b) by 1226 days.

(21) Appl. No.: 14/411,362

(22) PCT Filed: Dec. 26, 2012

(86) PCT No.: PCT/US2012/071662
§ 371 (c)(1),
(2) Date: Dec. 24, 2014

(87) PCT Pub. No.: WO2013/101836
PCT Pub. Date: Jul. 4, 2013

(65) Prior Publication Data
US 2015/0182134 A1 Jul. 2, 2015

Related U.S. Application Data

(60) Provisional application No. 61/717,325, filed on Oct. 23, 2012, provisional application No. 61/631,286, filed on Dec. 31, 2011.

(51) Int. Cl.
A61B 5/02 (2006.01)
C12Q 1/56 (2006.01)
(Continued)

(52) U.S. Cl.
CPC .......... *A61B 5/02042* (2013.01); *A61B 5/021* (2013.01); *A61B 5/02028* (2013.01);
(Continued)

(58) Field of Classification Search
CPC . A61B 5/02042; A61B 5/6898; A61B 5/7246; A61B 5/02028; A61B 5/7282;
(Continued)

(56) References Cited

U.S. PATENT DOCUMENTS 6,645,768 B1 * 11/2003 Tejidor .................. G01N 33/86
435/13
8,008,086 B2 8/2011 Cohen et al.
(Continued)

FOREIGN PATENT DOCUMENTS

JP 2009-244027 A 10/2009
WO 2009153964 A1 12/2009

OTHER PUBLICATIONS

Adams, "Assessment of Thrombin Generation: Useful or Hype?", Semin Thromb Hemost 2009; 35(1): 104-110 (Abstract Only).*
(Continued)

*Primary Examiner* — Jacqueline Cheng
*Assistant Examiner* — Tho Tran
(74) *Attorney, Agent, or Firm* — Melissa Hunter-Ensor; Tari Mills; Greenberg Traurig, LLP

(57) ABSTRACT

Featured is a method for assessing risk of a patient condition. Such a method includes providing criteria that relate predetermined parameters to each other, inputting observations into given criterion and relating observations of one or more acquired parameters, and converging the given crite-
(Continued)

rion so as to provide an output representative of a patient condition. Such a method further includes translating the output into a visual form such as displaying the output on a display device.

9 Claims, 22 Drawing Sheets

(51) Int. Cl.
G01N 33/86 (2006.01)
A61B 5/021 (2006.01)
A61B 5/145 (2006.01)
A61B 5/00 (2006.01)

(52) U.S. Cl.
CPC ...... *A61B 5/14535* (2013.01); *A61B 5/14546* (2013.01); *A61B 5/4848* (2013.01); *A61B 5/7246* (2013.01); *A61B 5/7278* (2013.01); *A61B 5/7282* (2013.01); *A61B 5/742* (2013.01); *C12Q 1/56* (2013.01); *G01N 33/86* (2013.01); *G01N 2800/60* (2013.01)

(58) Field of Classification Search
CPC ..... A61B 5/7278; A61B 5/4848; A61B 5/021; A61B 5/742; A61B 5/14546; A61B 5/14535; G01N 33/86; G01N 2800/60; C12Q 1/56

USPC ........................................................ 205/792
See application file for complete search history.

(56) References Cited

U.S. PATENT DOCUMENTS

| 2005/0130230 | A1* | 6/2005 | Davalos | G01N 33/6848 |
| | | | | 435/7.1 |
| 2008/0038276 | A1* | 2/2008 | Sinha | C07D 207/34 |
| | | | | 424/146.1 |
| 2009/0214485 | A1* | 8/2009 | Gavrilova | A61K 35/28 |
| | | | | 424/93.7 |
| 2009/0311730 | A1* | 12/2009 | Hemker | C12Q 1/56 |
| | | | | 435/13 |
| 2011/0252352 | A1 | 10/2011 | Viola et al. | |
| 2012/0178114 | A1* | 7/2012 | Owen | C12Q 1/37 |
| | | | | 435/13 |
| 2012/0208759 | A1* | 8/2012 | Fima | C07K 14/505 |
| | | | | 514/13.7 |
| 2012/0270789 | A1* | 10/2012 | Petersen | A61K 38/366 |
| | | | | 514/14.7 |

OTHER PUBLICATIONS

International Preliminary Report on Patentability and Written Opinion in corresponding PCT/US2012/071662, dated Jul. 1, 2014 (7 page).

* cited by examiner

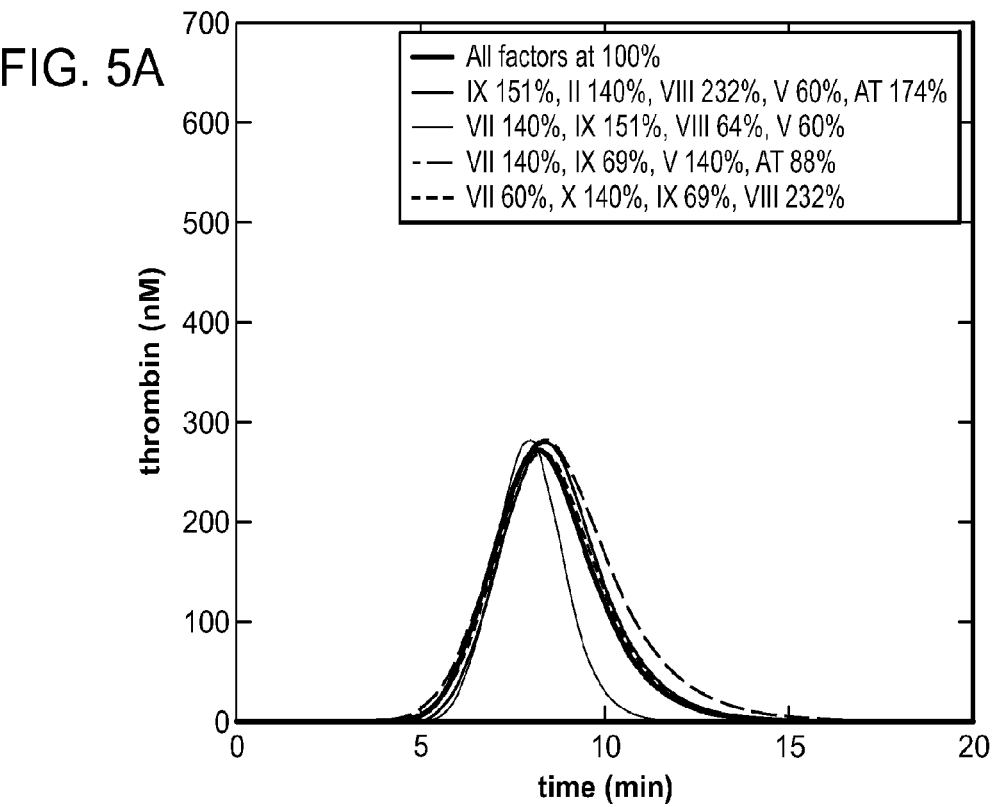
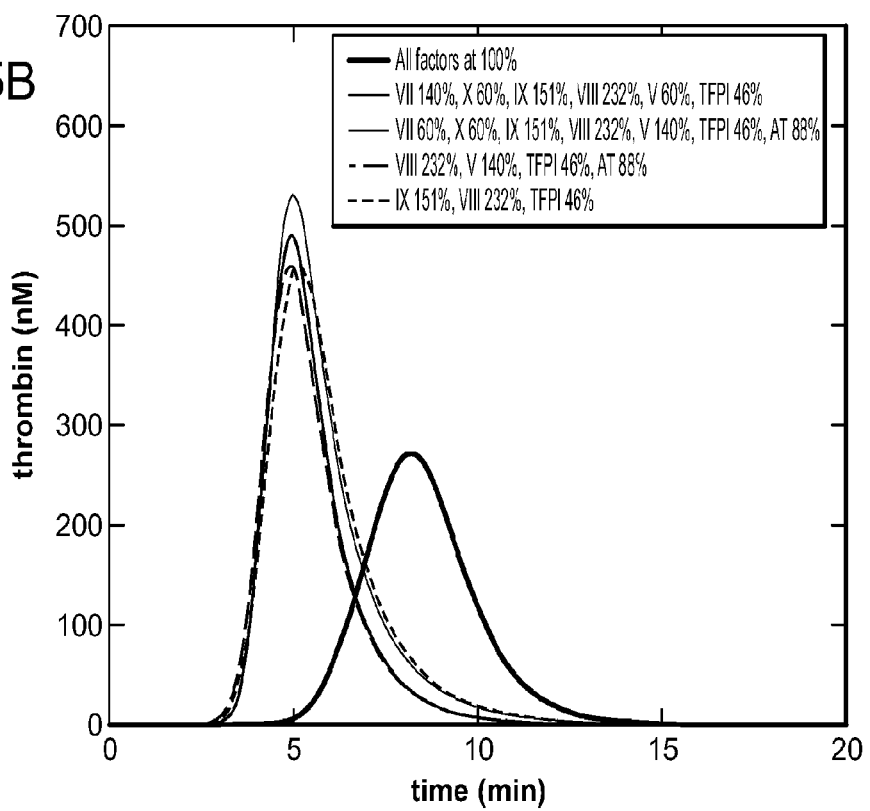

$$\frac{d[TF]}{dt} = -k_2[TF][VII] + k_1[TF=VII] - k_4[TF][VIIa] + k_3[TF=VIIa] \tag{1}$$

$$\frac{d[VII]}{dt} = -k_2[TF][VII] + k_1[TF=VII] - k_5[TF=VIIa][VII] - k_6[Xa][VII] - k_7[IIa][VII] \tag{2}$$

$$\frac{d[TF=VII]}{dt} = -k_1[TF=VII] + k_2[TF][VII] \tag{3}$$

$$\frac{d[VIIa]}{dt} = -k_4[TF][VIIa] + k_3[TF=VIIa] + k_5[TF=VIIa][VII] + k_6[Xa][VII] + k_7[IIa][VII] \tag{4}$$

$$\frac{d[TF=VIIa]}{dt} = -k_3[TF=VIIa] + k_4[TF][VIIa] - k_9[TF=VIIa][X] + k_8[TF=VIIa=X] - k_{12}[TF=VIIa][Xa] + k_{11}[TF=VIIa=Xa] \tag{5}$$

$$-k_{14}[TF=VIIa][IX] + k_{13}[TF=VIIa=IX] + k_{15}[TF=VIIa=IX] - k_{37}[TF=VIIa][Xa=TFPI] - k_{42}[TF=VIIa][AT]$$

$$\frac{d[Xa]}{dt} = -k_{12}[TF=VIIa][Xa] + k_{11}[TF=VIIa=Xa] + k_{22}[IXa=VIIIa=X] - k_{28}[Xa][Va] + k_{27}[Xa=Va] - k_{34}[Xa][TFPI] \tag{6}$$

$$+k_{33}[Xa=TFPI] - k_{38}[Xa][AT] + k_{43}[IXa][X]$$

$$\frac{d[IIa]}{dt} = -k_{16}[Xa][II] + k_{32}[mIIa][Xa=Va] - k_{41}[IIa][AT] \tag{7}$$

$$\frac{d[X]}{dt} = -k_9[TF=VIIa][X] + k_8[TF=VIIa=X] - k_{21}[IXa=VIIIa][X] + k_{20}[IXa=VIIIa=X] + k_{25}[IXa=VIIIa=X][X] - k_{43}[IXa][X] \tag{8}$$

$$\frac{d[TF=VIIa=X]}{dt} = k_9[TF=VIIa][X] - k_{10}[TF=VIIa=X] - k_8[TF=VIIa=X] \tag{9}$$

$$\frac{d[TF=VIIa=Xa]}{dt} = k_{10}[TF=VIIa=X] + k_{12}[TF=VIIa][Xa] - k_{11}[TF=VIIa=Xa] - k_{36}[TF=VIIa=Xa][TFPI] + k_{35}[TF=VIIa=Xa=TFPI] \tag{10}$$

$$\frac{d[IX]}{dt} = -k_{14}[TF=VIIa][IX] + k_{13}[TF=VIIa=IX] \tag{11}$$

$$\frac{d[TF=VIIa=IX]}{dt} = k_{14}[TF=VIIa][IX] - k_{13}[TF=VIIa=IX] - k_{15}[TF=VIIa=IX] \tag{12}$$

$$\frac{d[IXa]}{dt} = k_{15}[TF=VIIa=IX] - k_{19}[VIIIa][IXa] + k_{18}[IXa=VIIIa] + k_{25}[IXa=VIIIa=X] - k_{25}[IXa=VIIIa] - k_{40}[IXa][AT] \tag{13}$$

$$\frac{d[II]}{dt} = -k_{16}[Xa][II] - k_{30}[Xa=Va] + k_{29}[Xa=Va=II] \tag{14}$$

$$\frac{d[VIII]}{dt} = -k_{17}[IIa][VIII] \tag{15}$$

FIG. 14A $$\frac{d[VIIIa]}{dt} = k_{17}[IIa][VIII] - k_{19}[VIIIa][IXa] + k_{18}[IXa{=}VIIIa] - k_{24}[VIIIa] + k_{23}[VIII.ical{=}X][VIII.a2] \quad (16)$$

$$\frac{d[IXa{=}VIIIa]}{dt} = k_{19}[VIIIa][IXa] - k_{18}[IXa{=}VIIIa] - k_{21}[IXa{=}VIIIa][X] + k_{20}[IXa{=}VIIIa{=}X] + k_{22}[IXa{=}VIIIa{=}X] - k_{25}[IXa{=}VIIIa] \quad (17)$$

$$\frac{d[IXa{=}VIIIa{=}X]}{dt} = k_{21}[IXa{=}VIIIa][X] - k_{20}[IXa{=}VIIIa{=}X] - k_{22}[IXa{=}VIIIa{=}X] - k_{25}[IXa{=}VIIIa{=}X] \quad (18)$$

$$\frac{d[VIIIa.ical]}{dt} = k_{24}[VIIIa] + k_{25}[IXa{=}VIIIa{=}X] + k_{25}[IXa{=}VIIIa] - k_{23}[VIII.ical][VIIIa2] \quad (19)$$

$$\frac{d[VIIIa2]}{dt} = k_{24}[VIIIa] + k_{25}[IXa{=}VIIIa{=}X] + k_{25}[IXa{=}VIIIa] - k_{23}[VIII.ical][VIIIa2] \quad (20)$$

$$\frac{d[V]}{dt} = -k_{26}[IIa][V] - k_{44}[mIIa][V] \quad (21)$$

$$\frac{d[Va]}{dt} = k_{26}[IIa][V] - k_{28}[Xa][Va] + k_{27}[Xa{=}Va] + k_{44}[mIIa][V] \quad (22)$$

$$\frac{d[Xa{=}Va]}{dt} = k_{28}[Xa][Va] - k_{27}[Xa{=}Va] - k_{30}[Xa{=}Va][II] + k_{29}[Xa{=}Va{=}II] + k_{31}[Xa{=}Va{=}II] \quad (23)$$

$$\frac{d[Xa{=}Va{=}II]}{dt} = k_{30}[Xa{=}Va][II] - k_{29}[Xa{=}Va{=}II] - k_{31}[Xa{=}Va{=}II] \quad (24)$$

$$\frac{d[mIIa]}{dt} = k_{31}[Xa{=}Va{=}II] - k_{32}[mIIa][Xa{=}Va] - k_{39}[mIIa][AT] \quad (25)$$

$$\frac{d[TFPI]}{dt} = -k_{34}[Xa][TFPI] + k_{33}[Xa{=}TFPI] - k_{36}[TF{=}VIIa{=}Xa][TFPI] + k_{35}[TF{=}VIIa{=}Xa{=}TFPI] \quad (26)$$

$$\frac{d[Xa{=}TFPI]}{dt} = k_{34}[Xa][TFPI] - k_{33}[Xa{=}TFPI] - k_{37}[TF{=}VIIa][Xa{=}TFPI] \quad (27)$$

$$\frac{d[TF{=}VIIa{=}Xa{=}TFPI]}{dt} = k_{36}[TF{=}VIIa{-}Xa][TFPI] - k_{35}[TF{=}VIIa{=}Xa{=}TRPI] + k_{37}[TF{=}VIIa][Xa{=}TFPI] \quad (28)$$

$$\frac{d[AT]}{dt} = -k_{38}[Xa][AT] - k_{39}[mIIa][AT] - k_{40}[IXa][AT] - k_{41}[IIa][AT] - k_{42}[TF{=}VIIa][AT] \quad (29)$$

$$\frac{d[Xa{=}AT]}{dt} = k_{38}[Xa][AT] \quad (30)$$

$$\frac{d[mIIa{=}AT]}{dt} = k_{39}[mIIa][AT] \quad (31)$$

$$\frac{d[IXa{=}AT]}{dt} = k_{40}[IXa][AT] \quad (32)$$

$$\frac{d[IIa{=}AT]}{dt} = k_{41}[IIa][AT] \quad (33)$$

$$\frac{d[TF{=}VIIa{=}AT]}{dt} = k_{42}[TF{=}VIIa][AT] \quad (34)$$

FIG. 14B

METHODS FOR DYNAMIC VISUALIZATION OF CLINICAL PARAMETERS OVER TIME

RELATED APPLICATIONS

This application is the national phase under 35 U.S.C. § 371 of PCT International Application No. PCT/US2012/071662, filed Dec. 26, 2012, which claims the benefit of and priority to U.S. Provisional Patent Application No. 61/631,286, filed Dec. 31, 2011, and U.S. Provisional Patent Application 61/717,325, filed Oct. 23, 2012, the contents of which are incorporated herein by reference.

STATEMENT REGARDING FEDERALLY-SPONSORED RESEARCH

The present invention was supported by grants from the National Institute of Health, grant number HL46703. The U.S. Government has certain rights to the present invention.

BACKGROUND OF THE INVENTION

The coagulation of blood is the initial phase of the biological repair process that responds to perforating trauma to the vasculature; its function is to stop blood loss from the circulatory system by establishing a temporary barrier between the intra- and extra-vascular compartments. Relatively unique levels of detail are available for this biological network concerning its cellular and protein components, connections between these components, and the dynamics characterizing their interactions. Because of this, descriptions of this overall reaction network have been advanced using ensembles of ordinary differential equations (ODEs) or more elaborate mathematical constructs for both closed and flow based model systems.

Dynamic coagulation reactions are always characterized in terms of separate metrics like rates, reaction extents and timing of events. There are a number of instrument based methods, such as for example thromboelastograhy and calibrated automated thrombography, that are marketed to access the coagulation status of patients. Many of these instruments provide a global assessment of a single coagulation profile (e.g., thrombin output) of individuals, but the data needs to broken down to specific metrics, each representing a fraction of the available information to compare individuals. This approach of data analysis complemented with standard statistical methods has made limited progress in identifying at risk individuals.

It thus would be desirable to provide new methods and systems that improve the resolving power of current methods that evaluate blood coagulation dynamics. It would be particularly desirable to provide such methods and systems where multiple selected measures characterizing individual coagulation profiles are integrated so as to provide an improved level of resolving power with respect to the differences between individuals including the potential for risk assessment of hemorrhagic and thrombotic events and the monitoring of anticoagulation. It also would be particularly desirable to provide such methods and systems in which multiple measures from any of a number of instruments known in the art (such as those identified above) and values from standard clinical tests (e.g., prothrombin time (PT), activated partial thromboplastin time (aPTT)) can be repackaged, converted or the like into an integrated form that allows direct comparison to other individuals that are evaluated the same way. Additionally, it would be particularly desirable to provide such methods and systems that yield a visualization tool that represent the status of an individual's coagulation system, which in turn can allow monitoring and the visualization of an individual's blood coagulation profile or phenotype over time, while under anticoagulation, during surgeries, or other therapeutic interventions.

SUMMARY OF THE INVENTION

In its broadest aspects, the present invention features a method for the dynamic visualization of a subject's condition such as for example, the propensity for blood clotting or bleeding, and/or monitoring of therapeutics.

In one aspect, the invention provides a method for assessing hemostatic characteristics of a subject, the method involving the steps of providing criterion that relate one or more parameters to each other, the parameters including one or more selected from the group consisting of: clinical parameters, computationally-derived parameters of coagulation dynamics, empirical measures, and coagulopathies; inputting observations into given criterion and relating observations for one or more acquired parameters; and converging the given criterion so as to provide an output representative of hemostatic characteristics of a subject.

In one embodiment, the method further involves the step of translating the output into a visual form. In another embodiment, the step of translating includes displaying the output on a display device. In yet another embodiment, the display device is a hand held computer, smart phone, cellular telephone, tablet computer, or personal digital assistant. In yet another embodiment, the parameters are clinically or computationally derived thrombin parameters that characterize an individual's coagulant footprint. In yet another embodiment, the clinically, empirical, or computationally derived thrombin parameters are one or more of lag time, maximum rate of thrombin generation, peak thrombin and total thrombin/endogenous thrombin potential. In yet another embodiment, the clinical parameters are biomarker levels or activity, wherein the biomarker is selected from the group consisting of antithrombin III, activated partial thromboplastin time, blood pressure, body mass index, results of clot-based assays, clot elasticity, coagulation factors II, V, VII, VIIa, VIII, IX, X and Xa, D-dimer and fibrin degradation product levels, euglobulin clot lysis, estrogen levels, factor V Leiden, fibrin, fibrinolysis, fibrinogen activity, genetic mutation, heavy density lipoprotein levels, light density lipoprotein levels, patient age, plasma composition, platelet count, platelet function, red blood cells, tissue factor pathway inhibitor, protein C, protein S, plasminogen, prothrombin time, prothrombin ratio, results of a thrombin generation assay, smoking status, and results obtained from a calibrated automated thrombogram, thrombogram, or thromboelastography. In yet another embodiment, the clinical parameters further include patient data relating to bleeding score, drug dosages, drug metabolite levels, HIV status, inflammatory state, pregnancy or post-pregnancy status, and trauma. In yet another embodiment, the coagulopathy is hemophilia A, B, C, or von Willebrand's disease. In yet another embodiment, the criteria include one or more models or algorithms that relate observations of different parameters to each other. In yet another embodiment, the criteria include one or more models or algorithms that relate observations of integrated measures and clinical measures to each other. In yet another embodiment, the criteria include one or more sets of candidate models that each establish an algorithm that can infer relationships between the different measures. In yet another embodiment, the criteria include a set of candidate models at generation produced by selecting those candidate models with small residuals against the independent data and mutating them to produce a more diverse set and wherein the converging step includes, as the criterion approaches consensus on a structural form for the model, perturbing parameters relating the influence of each basis function until convergence is reached. In yet another embodiment, inputting observations includes inputting measures into an appropriate one of the one or more sets of candidate models. In yet another embodiment, the step of providing criteria includes identifying one or more parameters usable for defining normal or pathological states of hemostasis; and establishing criterion for relating acquired observations of the one or more acquired parameters.

In another aspect, the invention provides a non-transitory computer readable medium containing program instructions executable by a processor, the computer readable medium containing program instructions that provide criterion that relate one or more parameters to each other, the parameters including one or more selected from the group consisting of: clinical parameters, computationally-derived parameters of coagulation dynamics, and coagulopathies; program instructions that input observations into given criterion and relating observations for one or more acquired parameters; and program instructions that converge the given criterion so as to provide an output representative of propensity of the patient for blood clotting and bleeding. In another embodiment, the computationally-derived parameters of coagulation dynamics are one or more of time course of thrombin generation, computationally derived coagulation rate, lag time, maximum rate of thrombin generation, peak thrombin and total thrombin/endogenous thrombin potential, clinical parameters are biomarker levels or activity, wherein the biomarker is selected from the group consisting of antithrombin III, activated partial thromboplastin time, blood pressure, body mass index, results of clot-based assays, clot elasticity, coagulation factors II, V, VII, VIIa, VIII, IX, X and Xa, D-dimer and fibrin degradation product levels, euglobulin clot lysis, estrogen levels, fibrin, fibrinolysis, fibrinogen activity, heavy density lipoprotein levels, light density lipoprotein levels, factor V Leiden, patient age, plasma composition, platelet function, red blood cells, tissue factor pathway inhibitor, protein C, protein S, plasminogen, prothrombin time, prothrombin ratio, results of a thrombin generation assay, and results obtained from a calibrated automated thrombogram, thrombogram, or thromboelastography, or clinical thrombin parameters are one or more of lag time, maximum rate of thrombin generation, peak thrombin and total thrombin/endogenous thrombin potential; and the coagulopathy is hemophilia A, B, or C, or von Willebrand's disease.

In such a method, criteria are established so that selected parameters that can define the normal or pathologic states of such a condition can be related to each other such that when data, information or observations of such parameters are inputted and processed through such criteria, an output is provided which can then be displayed or visualized by clinician or technician so as to allow the clinician to assess and visualize how a subject's key clinical parameters change over time. A rapid understanding of how a subject's condition changes over time will improve the clinician's ability to treat the subject.

Such a method also allows a historical file of the subject to be maintained so that the clinician can observe any changes over time of the patient condition. For example, if the subject's condition to be assessed is the propensity for blood clotting and/or bleeding an assessment can be made and visualized using the method of the present invention before and/or after the subject undergoes a surgical procedure.

The standard clinical coagulation assays, activated partial thromboplastin time (aPTT) and prothrombin time (PT), cannot predict thrombotic or bleeding risk. Since thrombin generation is central to haemorrhage control and when unregulated, is the most likely cause of thrombosis, thrombin generation assays have gained acceptance as "global assays" of haemostasis. These assays generate an enormous amount of data including four key thrombin parameters (lag time, maximum rate of thrombin generation, peak thrombin and total thrombin/endogenous thrombin potential) that may change to varying degrees over time in longitudinal studies. Currently, each thrombin parameter is averaged and presented individually in a table, bar graph or box plot; no method exists to visualize comprehensive thrombin generation data over time. To address this need, a method of the invention visualizes all four thrombin parameters simultaneously and can be animated to evaluate how an individuals' thrombin generating capacity changes over time. This aspect of the invention uses all thrombin parameters to intrinsically rank individuals based on their haemostatic status.

While the data presentation method of the invention can integrate any clinically relevant measurement over time, it is especially suited to evaluate an individual's thrombotic and bleeding risk during "normal" (e.g., pregnancy or aging) or therapeutic challenges to the haemostatic system. In certain embodiments of the invention, the effects of warfarin therapy, factor VIII prophylaxis for haemophilia A, and pregnancy on thrombin generation are visualized over time.

According to one aspect of the present invention, there is featured a method for assessing risk associated with a patient condition, that includes providing criteria that relate one or more predetermined parameters to each other and inputting observations into given criteria and relating observations for one or more acquired parameters. Such a method also includes converging the given criteria so as to provide an output representative of a patient's or individual's condition. Such a method further includes translating the output into in a visual form such as displaying the output on a display device.

In further embodiments, such providing one or more models or algorithms includes identifying a condition that is to be monitored, tracked or visualized; identifying one or more parameters usable for defining normal or pathological states of the identified condition and establishing criteria for relating acquired observations of the one or more acquired parameters.

In yet further embodiments, the one or more parameters includes parameters obtained from empirical means, integrated means and clinical means.

In the case where the patient condition being assessed is the propensity for blood clotting and/or bleeding, the one or more parameters includes parameters relating to coagulation factor compositions, computationally derived parameters of coagulation dynamics and coagulopathies. In addition, the one or more parameters can include parameters relating to measures from computational analyses, thrombin parameters or other clinical parameters (e.g., levels or activity of any one or more of the following antithrombin III, activated partial thromboplastin time, blood pressure, body mass index, results of clot-based assays, clot elasticity, coagulation factors II, V, VII, VIIa, VIII, IX, X and Xa, Leiden factor V, D-dimer and fibrin degradation product levels, euglobulin clot lysis, estrogen levels, fibrin, fibrinolysis, fibrinogen activity, genetic mutations, heavy density lipoprotein levels, light density lipoprotein levels, patient age, plasma composition, platelet count, platelet function, red blood cells, tissue factor pathway inhibitor, protein C, protein S, plasminogen, prothrombin time, prothrombin ratio, results of a thrombin generation assay, and results obtained from a calibrated automated thrombogram, thrombogram, or thromboelastography, patient data relating to age, weight, bleeding score, drug dosages, drug metabolite levels, HIV status, inflammatory state, pregnancy or post-pregnancy status, smoking status, and trauma) that characterize an individual's coagulant footprint.

When the patient condition to be assessed is the propensity for blood clotting and/or bleeding, the one or more parameters includes parameters relating to clinically available data including lab measures, inflammatory state, bleeding score, and HIV status.

When the patient condition to be assessed is the propensity for blood clotting and/or bleeding, the empirical measures includes factor and hormone levels; integrated measures include thrombin, fXa, and plasmin generation and clinical measures include blood pressure (BP) pathology, anticoagulation, or bleeding score.

In yet further embodiments, said establishing criteria includes establishing one or more models or algorithms that relate observations of different parameters to each other. In particular, said establishing criteria can include establishing one or more models or algorithms that relate observations of empirical measures, integrated measures and clinical measures to each other. In further embodiments, said establishing criteria includes establishing one or more sets of candidate models that each establish an algorithm that can infer relationships between the different measures.

In yet further embodiments, said establishing criteria further includes repetitively generating sets of candidate models each of which relates the observations to each other, and then selecting those with small residuals against the independent data and then mutating them to produce a more diverse set. Models that don't perform well are culled. As the fitness of the candidate models improves, the algorithm approaches consensus on a structural form for the model that best describes the individual.

In yet further embodiments, said inputting of observations includes, inputting measures into one or more sets of candidate models.

According to another aspect of the present invention there is featured a method for assessing risk of the propensity of a patient/individual for blood clotting and/or bleeding. Such a method includes providing criteria that relate one or more predetermined parameters to each other, the parameters being related to coagulation factor compositions, computationally derived parameters of coagulation dynamics and coagulopathies; inputting observations into given criteria and relating observations for one or more acquired parameters; and converging the given criteria so as to provide an output representative of a patient condition. In embodiments of the present invention such a method also includes outputting the output in a visual form such as displaying the output on a display device.

In further embodiments, such providing includes providing one or models or algorithms that identify one or more parameters usable for defining normal or pathological states of blood clotting and/or bleeding; and establishing criteria for relating acquired observations of the one or more acquired parameters.

In yet further embodiments, the one or more parameters includes parameters relating to coagulation factor compositions, computationally derived parameters of coagulation dynamics and coagulopathies.

In yet further embodiments, the one or more parameters includes parameters relating to measures from computational analyses, thrombin parameters or other clinical parameters (e.g., levels or activity of any one or more of the following antithrombin III, activated partial thromboplastin time, blood pressure, body mass index, results of clot-based assays, clot elasticity, coagulation factors II, V, VII, VIIa, VIII, IX, X and Xa, Leiden factor V, D-dimer and fibrin degradation product levels, euglobulin clot lysis, estrogen levels, fibrin, fibrinolysis, fibrinogen activity, genetic mutations, heavy density lipoprotein levels, light density lipoprotein levels, patient age, plasma composition, platelet count, platelet function, red blood cells, tissue factor pathway inhibitor, protein C, protein S, plasminogen, prothrombin time, prothrombin ratio, results of a thrombin generation assay, and results obtained from a calibrated automated thrombogram, thrombogram, or thromboelastography patient data relating to age, weight, bleeding score, drug dosages, drug metabolite levels, HIV status, inflammatory state, pregnancy or post-pregnancy status, smoking status, and trauma) that characterize an individual's coagulant footprint.

In yet further embodiments, the one or more parameters include parameters obtained from empirical means, integrated means and clinical means. The parameters obtained from clinical means include parameters relating to clinically available data including lab measures (e.g., biomarkers PT, aPTT, thrombograms, thrombelastography), inflammatory state, bleeding score, level of anticoagulants and HIV status; the parameters obtained from empirical means includes factor and hormone levels; and the parameters obtained from integrated measures include thrombin, fXa, and plasmin generation.

According to yet other aspects of the present invention the above described methods are implemented or carried out on a computer as well as applications programs including instructions, criteria and code segments for performing the methods of the present invention.

Other aspects and embodiments of the invention are discussed below.

Definitions

As used herein, the term "dynamic visualization" means a method of visualizing the changes in multiple clinical parameters over time.

As used in the specification and claims, the singular form "a", "an" and "the" include plural references unless the context clearly dictates otherwise.

As used herein, the term "comprising" or "including" is intended to mean that the compositions, methods, devices, apparatuses and systems include the recited elements, but do not exclude other elements. "Consisting essentially of", when used to define compositions, devices, apparatuses, systems, and methods, shall mean excluding other elements of any essential significance to the combination. Embodiments defined by each of these transition terms are within the scope of this invention.

The term "individual" shall be understood to include a patient or human being, whether healthy or sick.

The term "patient" shall be understood to include mammalians including human beings or individuals, as well as other members of the animal kingdom, whether healthy or sick.

By "criteria" and "criterion" is meant models, algorithms and the like established so that observations (e.g., data, information) of the different parameters or the empirical measures, the integrated measures and the clinical measures can be related to each other.

By "parameter" is meant a variable that is indicative of a biological or clinical state. Examples of thrombin parameters are lag time, maximum rate of thrombin generation, peak thrombin, total thrombin/endogenous thrombin potential. In one embodiment, a parameter of the invention is the results of a coagulation factor test (Factors I-XII). In particular, a test for levels or activity of one or more of factors II, V, VII, VIIa, VIII, IX, X or Xa. In other embodiments, the parameters are clinical measures of a biomarker.

By "biomarker" is meant any clinical indicator relevant to the status of a subject. For example, biomarkers include the level or activity of any one of antithrombin III, activated partial thromboplastin time, blood pressure, body mass index, results of clot-based assays, coagulation factors II, V, VII, VIIa, VIII, IX, X and Xa, D-dimer and fibrin degradation product levels, euglobulin clot lysis, estrogen levels, fibrin, fibrinolysis, fibrinogen activity, genetic mutations, heavy density lipoprotein levels, light density lipoprotein levels, red blood cells, plasma composition, platelet count, platelet function, tissue factor pathway inhibitor, protein C, protein S, plasminogen, prothrombin time, prothrombin ratio, results of a thrombin generation assay, and results obtained from a calibrated automated thrombogram, thrombogram, or thromboelastography. Other biomarkers include subject data (e.g., subject age, weight, bleeding score, drug dosages administered, drug metabolite levels in blood, plasma, or serum, HIV status, inflammatory state, pregnancy or post-pregnancy status, patient history, smoking status, and trauma).

As used in the specification and claims the term "cTGP" shall be understood to mean computationally derived thrombin generation profile and the term cTGPS shall be understood to mean computationally derived thrombin generation profiles.

A "computer readable medium" shall be understood to mean any article of manufacture that contains data that can be read by a computer (non-transitory media) or a carrier wave signal carrying data that can be read by a computer. Such computer readable media includes but is not limited to magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or on carrier wave signal received through a network, wireless network or modem, including radio-frequency signals and infrared signals.

"USP" shall be understood to mean U.S. Patent Number, namely a U.S. patent granted by the U.S. Patent and Trademark Office.

BRIEF DESCRIPTION OF THE DRAWINGS

For a fuller understanding of the nature and desired objects of the present invention, reference is made to the following detailed description taken in conjunction with the accompanying drawing figures wherein like reference character denote corresponding parts throughout the several views and wherein:

FIGS. 5A-C are graphical figures of thrombin generation time courses from selected individuals from an hypothetical population defined by normal range variation in factors. Individuals were selected with disparate factor composition, but similar thrombin generation profiles and compared to an individual (control) with all factor levels at their mean physiologic value. Insets detail factor composition (as percentage of mean physiologic) which is variable among these individuals, with all other factors that are not listed at mean physiologic values. In FIG. 5A, there are 4 individuals similar to the control profile; FIG. 5B there are 4 individuals with accelerated and more robust thrombin generation relative to the control; and FIG. 5C there are 4 individuals with suppressed and delayed thrombin generation relative to the control.

8A depicts 16 individuals with severe hemophilia A (fVIII: 0.07% to 1% mean physiologic) and FIG. 8B depicts 65 individuals stably anticoagulated with warfarin (INR values between 2 and 3.3). The three individuals who subsequently had a thrombotic event are circled. FIG. 8C depicts a region of the hypothetical population distribution displaying the most similar thrombin generation parameters; the boundaries of the distributions of the hemophilia (green) and warfarin populations (pink+cyan (3 individuals)).

FIG. 14 provides a listing or tabulation of the ordinary differential equations that comprise the model described in Example 1.

DETAILED DESCRIPTION OF THE INVENTION

The invention generally features a method for dynamically visualizing multiple clinical parameters from a subject. While the data presentation technique of the invention can integrate any clinically relevant measurement over time, it is especially suited to evaluate a subject's thrombotic and bleeding risk during "normal" (e.g., pregnancy or aging) or therapeutic challenges to the haemostatic system.

For example, in one aspect of the invention, the temporal changes of all four of a subject's thrombin parameters are simultaneously presented and used to evaluate how the subject's thrombin generating capacity changes over time. This aspect of the invention uses all thrombin parameters to intrinsically rank subjects based on their haemostatic status. In certain embodiments of the invention, the effects of warfarin therapy, factor VIII prophylaxis for haemophilia A, and pregnancy on thrombin generation over time are visualized.

The standard clinical coagulation assays, activated partial thromboplastin time (aPTT) and prothrombin time (PT), cannot predict thrombotic or bleeding risk. Since thrombin generation is central to haemorrhage control and when unregulated, is the most likely cause of thrombosis, thrombin generation assays have gained acceptance as "global assays" of haemostasis. These assays generate an enormous amount of data including four key thrombin parameters (lag time, maximum rate of thrombin generation, peak thrombin and total thrombin/endogenous thrombin potential) that may change to varying degrees over time in longitudinal studies. Currently, each thrombin parameter is averaged and presented individually in a table, bar graph or box plot. The method of the invention provides a novel means to visualize comprehensive thrombin generation data over time.

The method of the invention has clear advantages over currently used data presentation techniques which describe thrombin generation parameters. Typically, these values are tabulated and reported as a mean±standard deviation or graphically each value is presented as bar graphs or box plots. In contrast, the invention features a unique and dynamic means of visualizing clinical data by providing a visual representation of all thrombin parameters in a single plot that captures how these parameters change over time in response to clinical events or therapies which alter a subject's haemostatic potential.

In one embodiment, the method of the invention was applied to three discrete populations with "abnormal" haemostasis thereby demonstrating the utility of the method in visualizing changes in thrombin generation during warfarin anticoagulation, fVIII prophylaxis for haemophilia A and pregnancy.

Figure 1:
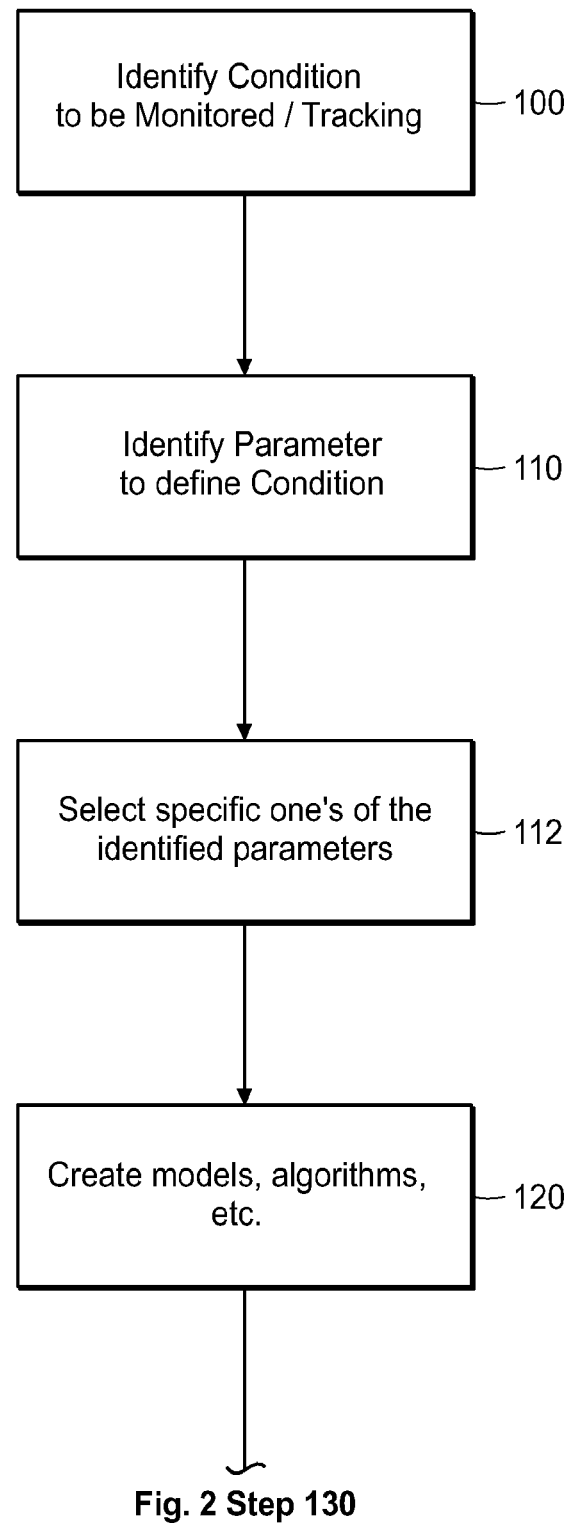
FIG. 1 is a high level flow diagram of methodology for creating one or more models that establish a relationship(s) between different types of parameters of an individual's or patient's condition being monitored and/or evaluated.
Figure 2:
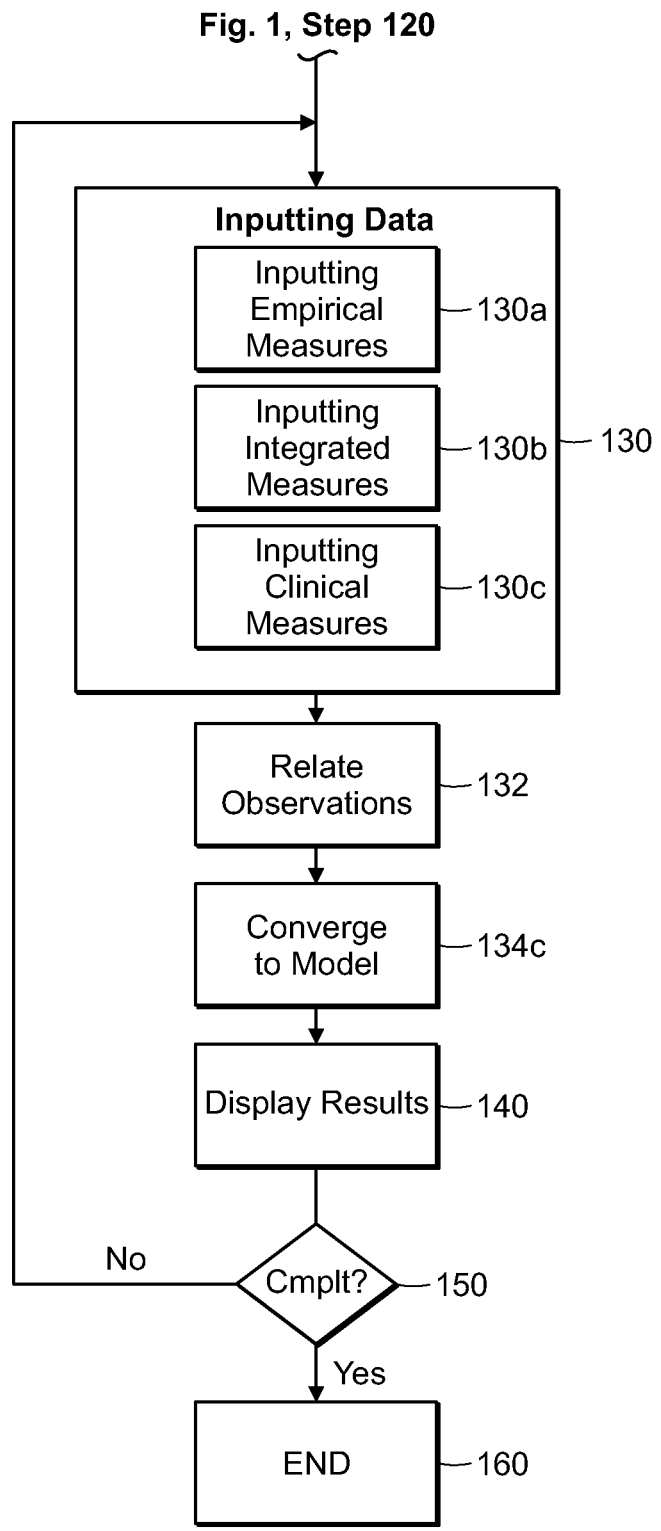
FIG. 2 is a high level flow diagram for using the one or more models created in FIG. 1 to develop a model associated with inputted data/parameters for the individual's or patient's condition being monitored and/or evaluated.

Referring now to the various figures of the drawing wherein like reference characters refer to like parts, there is shown in FIG. 1 a high level flow diagram of methodology for creating one or more models that establish a relationship(s) between different types of parameters of an individual's or patient's condition being monitored and/or evaluated. Also, there is shown in FIG. 2 a high level flow diagram for using the one or more models created in FIG. 1 to develop a model associated with inputted data/parameters for the individual's or patient's condition being monitored, tracked and/or evaluated. In further aspects, the process continues with displaying the model or results from the inputted data so that one can visualize the status of such a condition.

These flow charts also herein illustrate the structure of the logic of the different methodologies/inventions, which can be embodied in computer program software for execution on a computer, digital processor or microprocessor. Those skilled in the art will appreciate that the flow charts illustrate the structures of the computer program code elements, including logic circuits on an integrated circuit, that function according to the present inventions. As such, the present invention(s) may be practiced in its essential embodiments by a machine component that renders the program code elements in a form that instructs a digital processing apparatus (e.g., computer) to perform a sequence of function step(s) corresponding to those shown in the flow diagrams.

Referring now to FIG. 1, the process starts with identifying or determining the individual's or patient's condition that is to be monitored, tracked, assessed and/or evaluated. In a more particular or illustrative embodiment, the condition is an individuals' propensity towards bleeding or clotting or the individual's coagulation footprint, Step 100. While the following discussion describes the methods of the present invention in connection with various aspects or features associated with blood coagulation or anti-coagulation or a person's propensity towards clotting or bleeding, this shall not be construed as limiting the present invention to only methods for characterizing clotting or bleeding. As described further below, it is within the scope of the present invention to use the methods of the present invention to monitor and evaluate other conditions, such as for example lung function, liver function/disease, pharmacological intervention, toxico kinetic modeling, infectious disease, cancer, sickle cell disease, coronary changes, lupus, hepatitis, immunetolerance therapy, trauma, oral contraceptive use, whereby such a condition can be monitored and/or evaluated by relating parameters that are associated with such a condition, to each other in the fashion described herein.

After identifying or determining the individual's or patient's condition that is to monitored, tracked and/or evaluated, the process next identifies those parameters that can be utilized to define the normal and pathologic states of the identified condition, Step 110. These parameters can include those obtained from empirical means, integrated means and clinical means. In the case of blood clotting and/or bleeding these can include coagulation factor compositions, computationally derived parameters of coagulation dynamics (usually characterized in terms of metrics like rates, reaction extents and timing of events) and coagulopathies. This also includes measures from computational analyses, thrombin parameters or other clinical parameters (e.g., biomarkers) that characterize an individual's coagulant footprint as well as clinically available data such as lab measures, inflammatory state, bleeding score, HIV status. Also, empirical measures includes, e.g., factor and hormone levels; integrated measures include, e.g., levels or activity of any one or more of antithrombin III, activated partial thromboplastin time, blood pressure, body mass index, results of clot-based assays, coagulation factors II, V, VII, VIIa, VIII, IX, X and Xa, D-dimer and fibrin degradation product levels, euglobulin clot lysis, estrogen levels, fibrin, fibrinolysis, fibrinogen activity, genetic mutations, heavy density lipoprotein levels, light density lipoprotein levels, red blood cells, plasma composition, platelet count, platelet function, tissue factor pathway inhibitor, protein C, protein S, plasminogen, prothrombin time, prothrombin ratio, results of a thrombin generation assay, and results obtained from a calibrated automated thrombogram, thrombogram, or thromboelastography, thrombin, plasmin generation) and clinical measures include, e.g., patient data relating to bleeding score, drug dosages, drug metabolite levels, HIV status, inflammatory state, pregnancy or post-pregnancy status, trauma, blood pressure (BP) pathology, anticoagulation, or bleeding score. From this set of identified parameters, at least selected ones of such parameters are identified specifically for such monitoring and inputting of data/information, Step 112.

Next, criteria/criterion in the form of models, algorithms and the like are established so that observations (e.g., data, information) of the different parameters or the empirical measures, the integrated measures and the clinical measures can be related to each other, Step 120. In particular embodiments, a set of candidate models are established relating observations to each other as well as consisting of basis functions involving state variables and operators for combining them. In more particular embodiments, such a set(s) of candidate models establish an algorithm that can infer relationships between the different measures (e.g., blood composition, integrated measures and clinical hemostatic phenotype). In yet more particular embodiments, a set of candidate models are chosen at generation by selecting those with small residuals against the independent data and mutating them to produce a more diverse set. As the fitness of the candidate models improves, the algorithm approaches consensus on a structural form for the model and begins to perturb parameters relating the influence of each basis function until convergence is reached.

After establishing the set of candidate models and the like, the process proceeds to the use of such models, algorithms and the like in connection with the monitoring, tracking and/or evaluating of the identified condition for a given individual or patient, Step 130, FIG. 2. In particular the process proceeds with the inputting of data into the model, algorithm or the like for further processing, Step 130. In more specific embodiments, such inputting of data includes the inputting of empirical measures/data/information, Step 130a, inputting of integrated measures/data/information, Step 130b or inputting of clinical measures/data/information, Step 130b. In this regard, such inputting includes directed inputting of such measures/data from a device or apparatus (such as those herein described) that generates the data/measure. Alternatively, such data, measure or information is outputted by another applications program into the device/apparatus executing the methodology of the present invention.

After such inputting, the process proceeds with relating the observations (i.e., inputted measures, data or information) to each other and so as to converge them into a single model Steps 132, 134. As indicated herein, a set of candidate models are established relating observations to each other as well as consisting of basis functions involving state variables and operators for combining them. In more particular embodiments, such a set(s) of candidate models establish an algorithm that can infer relationships between the different measures (e.g., blood composition, integrated measures and clinical hemostatic phenotype). In yet more particular embodiments, a set of candidate models are chosen at generation by selecting those with small residuals against the independent data and mutating them to produce a more diverse set. As the fitness of the candidate models improves, the algorithm approaches consensus on a structural form for the model and begins to perturb parameters relating the influence of each basis function until convergence is reached.

Figure 3:
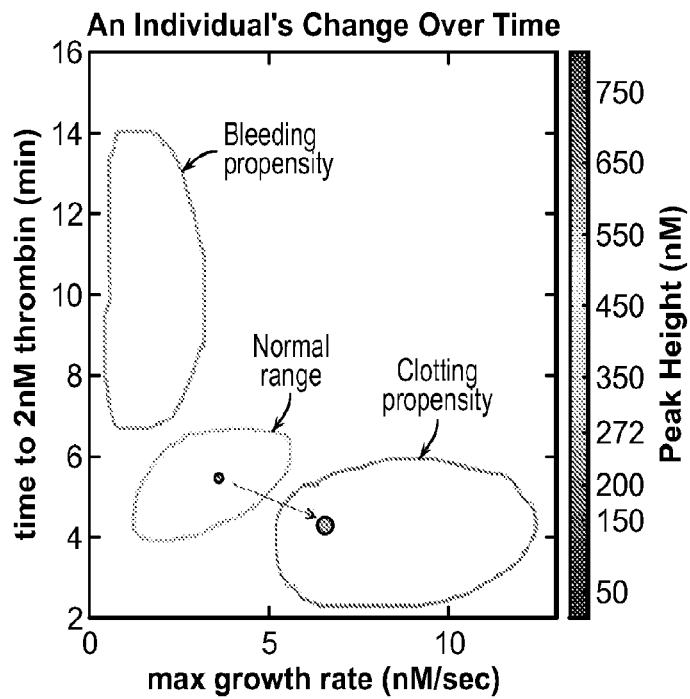
FIG. 3 is an illustrative graphical figure illustrating a visualization of the model of normal and/or pathologic states of an individual's or patient's condition being monitored/evaluated.

After convergence, the resultant data or model can be outputted to the user for monitoring, evaluation and tracking purposes of a given individual or patient. In more particular embodiments, the resultant data or model is displayed on a display device (e.g., liquid crystal type of display, CRT type of display, plasma type of display or any other display known in the art or hereinafter developed, Step 140. This also includes translating the resultant data or model so that such an output is suitable for visualizing or displaying. In this way, the clinician, technician or the like can visualize the condition being monitored, tracked or evaluated such as for example, the individual's or patient's propensity towards bleeding or clotting. An illustration of such a visual display is shown in FIG. 3.

Devices suitable for the display of data generated according to the method of the invention include small, hand-held computing devices having a display screen, a miniature keyboard and weighing less than 2 pounds. Such handheld devices include those manufactured by Apple, HTC, Samsung, LG, Research in Motion (RIM) and Motorola. Preferably, such devices have an operating system (OS) capable of running application software (e.g., apps). Preferably, such devices provide for wireless connection to the Internet (e.g., WI-FI, Bluetooth).

The process next determines, if the process is completed or not, Step 150. As indicated herein, the process can be continuous or done at predetermined times responsive to the acquisition of new measures, data or information. Thus, if the process is not complete (No, Step 150), then the process returns to Step 130 and thereafter Steps 132, 134 and 140 are repeated as and until the process is deemed or determined to be completed (Yes, Step 150). If the process is deemed or determined to be completed, then the process is ended, Step 160.

This process as set forth in Steps 130 through steps 150 also is repeated at another time, if re-starting of the process is deemed required due to the presence of new data, measure or information that needs to be processed. In this way, the clinician, doctor or the like can continue to monitor, track and evaluate an individual's or patient's condition over time and also before and/or after events in the individual's or patient's medical history. For example, an evaluation can be made before and/or after a surgical procedure is performed as well as after routine physical or medical examinations (e.g., mammograms).

Such methods of the present invention are suitable for use in combination with any of a number of computer systems as are known to those skilled in the art or hereinafter developed. Such a computer system includes a computer, a display, and one or more input device(s). The display is any of a number of devices known to those skilled in the art for displaying images responsive to outputs signals from the computer, including but not limited to cathode ray tubes (CRT), liquid crystal displays (LCDS), plasma screens and the like. It should be recognized that the signals being outputted from the computer can originate from any of a number of devices including PCI or AGP video boards or cards mounted with the housing of the computer that are operably coupled to the computer's microprocessor and the display.

The one or more input device(s) are any of a number of devices known to those skilled in the art which can be used to provide input signals to the computer for control of applications programs and other programs such as the operating system being executed within the computer. In illustrative embodiments, the input device preferably comprises a switch, a slide, a mouse, a track ball, a glide point or a joystick or other such device (e.g., a keyboard having an integrally mounted glide point or mouse) by which a user such as student can input control signals other than by means of a keyboard.

The computer typically includes a central processing unit including one or more micro-processors such as those manufactured by Intel or AMD, Motorola or the like, random access memory (RAM), mechanisms and structures for performing I/O operations, a storage medium such as a magnetic hard disk drive(s) or other drives (fixed or removable) for storage of data, operating systems or the applications or software programs of the present invention including an applications program according to the present invention(s), and a device (not shown) for reading from and/or writing to a removable computer readable medium, such as for example an optical disk reader capable of reading CDROM, DVD or optical disks and readers of other types of nonvolatile memory such as flash drives, jump drives or spin memory that embody one or more types of non-volatile types of memory or storage devices.

Such a hard disk drive is provided for purposes of booting and storing the operating system, other applications or systems that are to be executed on the computer, paging and swapping between the hard disk and the RAM and the like. In this embodiment, an applications program according to the present invention is stored in the hard drive including the programming instructions and a data portion containing the text, auditory and visual informational data being displayed as well as the historical file of such information. Such data also can be stored in a removable computer readable medium such as a CD or DVD type of media that is inserted into a device for reading and/or writing to the removable computer readable media. Such a reading/writing device is any of a number of devices known to those skilled in the art for reading from and/or writing to the particular medium on which the applications program is stored.

In an alternative embodiment, such a computer system also includes a network based computer system that includes a server, an external storage device and a network infrastructure that operably couples a plurality or more of client computer systems to the server. The client computer systems are typically configured like the above described computer system except that in use the applications program of the present invention and related data of a condition for a given individual could be found on the server 210 and such information would be temporarily onto the client computer system.

The server is any of a number of servers known to those skilled in the art that are intended to be operably connected to a network so as to operably link a plurality or more of client computers via the network to the server and thus also to the external storage device. Such a server typically includes a central processing unit including one or more microprocessors such as those manufactured by Intel or AMD, random access memory (RAM), mechanisms and structures for performing I/O operations, a storage medium such as a magnetic hard disk drive(s), and an operating system for execution on the central processing unit. The hard disk drive of the server typically is not used for storing data and the like utilized by client applications being executed on the client computers. Rather the hard disk drive(s) of the server are typically provided for purposes of booting and storing the operating system, other applications or systems that are to be executed on the server, paging and swapping between the hard disk and the RAM.

Data and the like being used in connection with the execution of client applications, such as the applications program of the present invention and the information and/or data related thereto, can be stored in the external storage device that is operably interconnected to the server using any of a number of techniques and related devices or cabling known to those skilled in the art. In an illustrative embodiment, such an interconnection is implemented using a small computer systems interface (SCSI) technique(s) or via a fiber optic cable or other high-speed type of interconnection.

In an illustrative, exemplary embodiment, the external storage device 260 comprises a disk assembly typically made up of one or more hard disks that are configured and arranged so the external storage medium functionally appears to the server as a single hard disk. Such an external storage medium is further configured and arranged to implement any of a number of storage schemes such as mirroring data on a duplicate disk (RAID level 1) or providing a mechanism by which data on one disk, which disk has become lost or inaccessible, can be reconstructed from the other disks comprising the storage medium (RAID level 5). Although reference is made to a disk assembly and hard disks, this is for illustration and shall not be construed as being a limitation on the particular form of the devices or mechanism that makes up the external storage device or the medium comprising such a device.

In addition, each of the client computers includes one or more I/O ports that are operably connected to the microprocessor and which are configured and arranged for the transfer of the data and program instructions between and amongst the client computer and the server using any of a number of non-wireless techniques or wireless techniques known to those skilled in the art. Such non-wireless techniques include for example any of a number of network infrastructures known to those skilled in the art such as Ethernet, token ring, FDDI, ATM, Sonet, X.25 and Broadband.

In the case of wireless techniques, the I/O ports of the client computers are configured so as to include a transceiver as is known to those skilled in the art for wireless network transmission systems. An exemplary wireless network technique includes those systems embodying a transceiver or transmitter complying with IEEE-802.11 or other appropriate standards hereinafter developed. In each case, the transceiver operably coupled to the client computer is configured and arranged so as to establish a communications link between the client computer and a receiver or transceiver remote from the location of the client computer that is in turn operably coupled to the server. The server in turn could be coupled to the remotely located transceiver/receiver using non-wireless or wireless techniques.

Example 1: Assessing Risk Associated with Individualized Blood Coagulation Profiles The coagulation of blood is the initial phase of the biological repair process that responds to perforating trauma to the vasculature; its function is to stop blood loss from the circulatory system by establishing a temporary barrier between the intra- and extra-vascular compartments. Relatively unique levels of detail are available for this biological network concerning its cellular and protein components, connections between these components, and the dynamics characterizing their interactions. Because of this, descriptions of this overall reaction network have been advanced using ensembles of ordinary differential equations (ODEs) (Hockin et al., (2002) J Biol Chem 277: 18322-18333; Panteleev et al., (2006) Biophys J 90: 1489-1500; Luan et al., (2007) PLoS Comput Biol 3: e142; Anand et al., (2008) J Theor Biol; Chatterjee et al., (2010) PLoS Comput Biol 6; Mitrophanov et al. (2011) Thrombosis research 128: 381-390) or more elaborate mathematical constructs for both closed and flow based model systems (Hall et al. (1998) Annals of biomedical engineering 26: 28-36; Kuharsky et al. (2001) Biophys J 80: 1050-1074; Ataullakhanov et al. (2005) Pathophysiol Haemost Thromb 34: 60-70; Fogelson (2005) Pathophysiol Haemost Thromb 34: 91-108; Anand et al. (2008) J Theor Biol 253: 725-738; Xu et al. (2008) J R Soc Interface 5: 705-722; Runyon et al. (2008) J Am Chem Soc 130: 3458-3464; Wajima et al. (2009) Clinical pharmacology and therapeutics 86: 290-298; Xu et al. (2011) Arterioscler Thromb Vasc Biol 31: 500-505).

The present work has focused on developing and validating an ODE-based description limited to the tissue factor (Tf) pathway to thrombin formation and then using this model in concert with empirical studies to develop concepts of normal and aberrant thrombin generation in individuals and populations with chronic or acute pathologies, as well as understanding mechanisms of anticoagulant efficacy.

An important issue in developing a predictive model of coagulation with clinical utility is the tension between the complexity of the model (its relative level of congruence with the biological network) and the capacity to measure the actual physiochemical parameters (i.e., initial concentrations of reactants and rate constants) governing the network. With respect to comparatively modeling the coagulation systems of individuals in the human population, the working assumption is that, in the absence of a specific mutation that alters the function of a key enzyme or substrate (e.g. factor (f)V Leiden), the rate constants are invariant. Thus measurement error in rate constants would be the primary source of uncertainty in their values (Danforth et al. (2009) Math Med Biol 26: 323-336). In contrast, the concept of initial species levels is complicated by issues beyond measurement uncertainty, including a lack of information or reasonable assessment methods concerning the in vivo concentrations (or surface level expression) of cellular components of the coagulation proteome and the fact that individuals are known to vary in concentrations of soluble coagulation factor precursors. A reasonable resolution of the conflict between model complexity and required input data is a precondition if one is aiming to develop a model that provides therapeutic guidance on an individual by individual basis.

One approach for modeling individuals has generally been to limit the description of the network to seven circulating precursor proteins (factors II, V, VII, VIIa, VIII, IX, X) and two inhibitors (antithrombin (AT), and tissue factor pathway inhibitor (TFPI)). The rationale for this has three parts: (1) These proteins appear to be central to the process of Tf initiated thrombin formation (Mann et al. (2009) Hamostaseologie 29: 7-16) and its regulation by anticoagulant agents. Absolute deficiencies in any of these are either incompatible with life, or result in bleeding disorders (fV, fX, prothrombin, fVIII, fIX or thrombosis (AT). Additionally, the importance of the four vitamin K dependent proteins (fII, fVII/VIIa, fIX and fX) to normal hemorrhage control is exemplified by their status as primary targets for the anticoagulants warfarin, both of which have been used for over 60 years. These two therapeutic agents mirror each other in the scope of their action, since UFH potentiates the inhibition of all of the procoagulant enzymes that warfarin anticoagulation targets indirectly by suppressing the levels of their functional precursors. (2) The magnitude of the normal range variation of these soluble proteins between individuals is greater than the measurement uncertainty for these proteins, a methodologic precondition for their use to discriminate among individuals. (3) The mathematical representation of the interactions of these proteins in the reaction network appears valid, based on the congruence between empirical reconstructions of this limited network and model descriptions (Hockin et al. (2002) J Biol Chem 277: 18322-18333; Orfeo et al. (2010) J Thromb Haemost 8: 1745-1753).

In this study, the initial protein concentrations in the empirically validated ODE based model of Tf-initiated blood coagulation were systematically perturbed, within the acceptable healthy clinical laboratory range, to evaluate the effect on thrombin generation. A unique graphical method is developed to integrate standard measures used to characterize thrombin generation in empirical and computational models (e.g., max rate, max level, total thrombin, time to 2 nM thrombin) to visualize how normal range variation in coagulation factors results in unique thrombin generation phenotypes. Four approaches are taken: (1) characterizing the possible range of thrombin generation phenotypes as a function of normal range variation in factor levels, i.e. defining the theoretical population range of the healthy coagulant response to Tf; (2) relating the thrombin generation profiles of apparently healthy and hemostatically challenged populations derived using their actual plasma coagulation factor composition to the theoretical "normal" population range; (3) systematically analyzing the sensitivity of model output of all species collectively and of thrombin specifically to normal range variation in each coagulation factor; and (4) relating the subset of factors for which model output is most sensitive to their normal range variation to the factor compositions that yield "abnormal" phenotypes.

Key findings of these analyses include that normal range variation of coagulation factors yields thrombin generation phenotypes indistinguishable from individuals with some but not all coagulopathies and that coordinate variation of certain pairs of factors disproportionately results in extreme thrombin generation phenotypes, implying that measurement of a smaller set of factors may be sufficient to identify individuals with aberrant thrombin generation potential. These novel types of analyses can ultimately be used to develop clinical tools to evaluate individual procoagulant potential.

Mathematical Model.

The current mathematical model of coagulation utilizes reactions described in publications by Hockin et al, infra and Butenas et al. (2004) J Biol Chem 279: 22875-22882, which are incorporated by reference, describing the dynamics of tissue factor (Tf) initiated blood coagulation. Inputs to the model include the concentrations of procoagulant factors II, V, VII/VIIa, VIII, IX, X and the anticoagulants TFPI and AT and the rate constants derived from experimental measurements made under conditions of saturating concentrations of phospholipids (Hockin et al, 2002, infra). The starting concentration of fVIIa was always 1% of the starting fVII concentration (xx). MatLabs stiff solver odel5s (Shampine L F, Reichelt M W (197) The MATLAB ODE Suite. SIAM Journal on Scientific Computing 18: 1-22) was used to integrate the ODE model with variable time steps whose maximum size was set to $5 \times 10^3$s. The model is initiated by exposing the inputs to 5 pM Tf and yields concentration versus time profiles for all of the 34 species representing reactants, intermediates or products. A listing or tabulation of the ordinary differential equations that comprise the model is provided in FIG. 14.

Populations

Thirty-two apparently healthy individuals recruited from hospital and university staff (Jagiellonian University Medical College, Krakow, Poland) served as controls. Warfarin treated individuals (N=65; 23 females, 42 males; age: 25-75 years) were apparently on stable anticoagulation (mean time of 4 months; 2≤INR≤3.3). Indications for vitamin K antagonist administration were atrial fibrillation (N=26), venous thromboembolism (N=25) or aortic prosthetic valve implantation (N=14). The exclusion criteria were recent (preceding 6 months) thromboembolic event, acute infection, liver injury, renal insufficiency, autoimmune disorders or known cancer. Three individuals had a thrombotic event subsequent to the blood draw for compositional analysis. Severe hemophilia A individuals (by diagnosis; N=16) displayed NIB levels ranging from not detectable to ≤1% at the time of the blood draw used for compositional analysis.

Modeling Thrombin Generation in Individuals:

Thrombin Generation Phenotypes.

Figure 4:
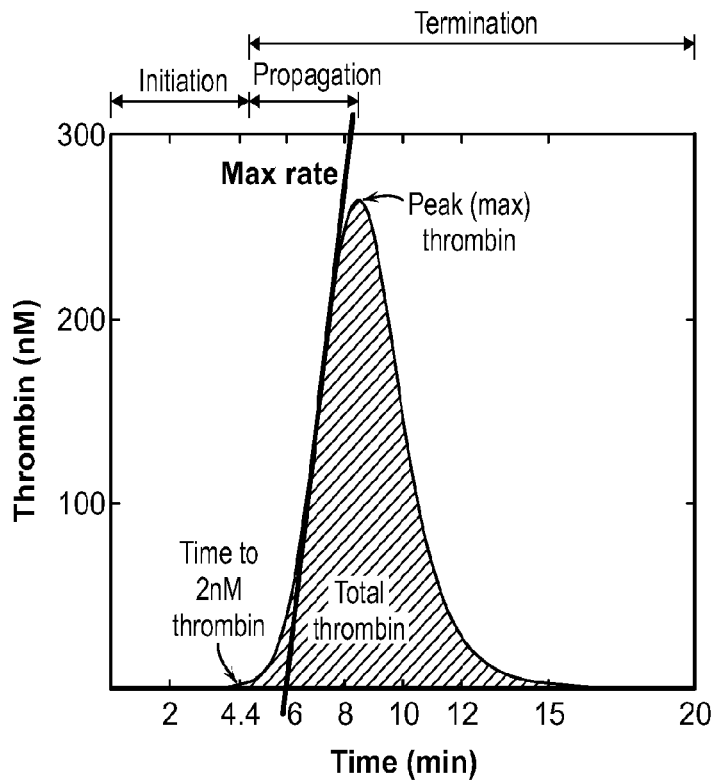
FIG. 4 is a graphical view of a thrombin generation profile reflecting the dynamics observed in a closed model system. A computationally-derived time course of thrombin generation with all factors at their mean physiologic level and a 5 pM tissue factor stimulus is shown. Also indicated are the thrombin parameters (time to 2 nM thrombin (clot-time), total thrombin, maximum thrombin, maximum rate) used in this analysis.

In empirical models, thrombin is the most common analyte both because of its ease of measurement and its central and diverse roles. Thrombin generation in these closed model systems displays three distinct phases: initiation of coagulation, propagation of α-thrombin formation, and termination of the procoagulant response (FIG. 4). Computationally derived thrombin generation profiles (cTGPs) were evaluated by standard summary measures that described each curve including the maximum level and rate of thrombin generation, total thrombin generated (the area under the curve) and the time to 2 nM active thrombin, which corresponds to clot time in our empirical studies (Brummel J T H 2005, infra). Collectively these 4 parameters are used to define a thrombin generation phenotype.

Thrombin Generation in a Hypothetical Normal Population.

To produce a representation of the distribution of possible thrombin generation phenotypes, the eight factors with non zero initial concentrations were varied across their normal range. This population of factor ensembles was produced by allowing each factor to have three possible normal range values: extreme low, mean physiologic (all factors at 100%) and extreme high, yielding ($3^8$) permutations (see Table 1) from each of which the four thrombin parameters were extracted.

TABLE 1

Hypothetical normal range plasma compositions resulting in extreme thrombin generation phenotypes. A rank ordering for each of the 6561 simulations for four metrics is show with the combination of initial factor concentrations that produced them.

| | % VII | % X | % IX | % II | % VIII | % V | % TFPI | % AT |
|---|---|---|---|---|---|---|---|---|
| Time to 2 nM IIa (min) | | | | | | | | |
| 2.30 | 140 | 140 | 151 | 140 | 232 | 140 | 46 | 88 |
| 2.35 | 140 | 100 | 151 | 140 | 232 | 140 | 46 | 88 |
| 2.38 | 140 | 140 | 151 | 100 | 232 | 140 | 46 | 88 |
| 2.40 | 140 | 140 | 151 | 140 | 232 | 100 | 46 | 88 |
| 2.42 | 140 | 100 | 100 | 140 | 232 | 140 | 46 | 88 |
| ... | ... | ... | ... | ... | ... | ... | ... | ... |
| 14.03 | 140 | 140 | 69 | 60 | 64 | 60 | 171 | 174 |
| 14.07 | 60 | 60 | 69 | 60 | 64 | 60 | 171 | 174 |
| 14.30 | 100 | 140 | 69 | 60 | 64 | 60 | 171 | 174 |
| 14.52 | 60 | 100 | 69 | 60 | 64 | 60 | 171 | 174 |
| 14.97 | 60 | 140 | 69 | 60 | 64 | 60 | 171 | 174 |
| Peak IIa (nM) | | | | | | | | |
| 792.4 | 140 | 60 | 151 | 140 | 232 | 60 | 46 | 88 |
| 790.9 | 140 | 60 | 151 | 140 | 232 | 100 | 46 | 88 |
| 789.8 | 100 | 60 | 151 | 140 | 232 | 60 | 46 | 88 |

TABLE 1-continued

Hypothetical normal range plasma compositions resulting in extreme thrombin generation phenotypes. A rank ordering for each of the 6561 simulations for four metrics is show with the combination of initial factor concentrations that produced them.

|  | % VII | % X | % IX | % II | % VIII | % V | % TFPI | % AT |
|---|---|---|---|---|---|---|---|---|
| 789.4 | 140 | 60 | 151 | 140 | 232 | 140 | 46 | 88 |
| 788.1 | 100 | 60 | 151 | 140 | 232 | 100 | 46 | 88 |
| ... | ... | ... | ... | ... | ... | ... | ... | ... |
| 25.0 | 140 | 140 | 69 | 60 | 64 | 60 | 171 | 174 |
| 24.7 | 60 | 140 | 69 | 60 | 64 | 140 | 171 | 174 |
| 24.6 | 100 | 140 | 69 | 60 | 64 | 60 | 171 | 174 |
| 24.4 | 60 | 140 | 69 | 60 | 64 | 100 | 171 | 174 |
| 23.7 | 60 | 140 | 69 | 60 | 64 | 60 | 171 | 174 |
| Max Rate (nM/sec) | | | | | | | | |
| 12.4 | 140 | 60 | 151 | 140 | 232 | 60 | 46 | 88 |
| 12.3 | 140 | 60 | 151 | 140 | 232 | 100 | 46 | 88 |
| 12.2 | 100 | 60 | 151 | 140 | 232 | 60 | 46 | 88 |
| 12.2 | 140 | 60 | 151 | 140 | 232 | 140 | 46 | 88 |
| 12.1 | 100 | 60 | 151 | 140 | 232 | 100 | 46 | 88 |
| ... | ... | ... | ... | ... | ... | ... | ... | ... |
| 0.112 | 140 | 140 | 69 | 60 | 64 | 60 | 171 | 174 |
| 0.110 | 100 | 140 | 69 | 60 | 64 | 60 | 171 | 174 |
| 0.107 | 60 | 140 | 69 | 60 | 64 | 140 | 171 | 174 |
| 0.106 | 60 | 140 | 69 | 60 | 64 | 100 | 171 | 174 |
| 0.103 | 60 | 140 | 69 | 60 | 64 | 60 | 171 | 174 |
| Total IIa (sec*nM) | | | | | | | | |
| 134338 | 140 | 60 | 151 | 140 | 232 | 60 | 46 | 88 |
| 134256 | 100 | 60 | 151 | 140 | 232 | 60 | 46 | 88 |
| 134239 | 140 | 60 | 151 | 140 | 232 | 100 | 46 | 88 |
| 134173 | 140 | 60 | 151 | 140 | 232 | 140 | 46 | 88 |
| 134146 | 100 | 60 | 151 | 140 | 232 | 140 | 46 | 88 |
| ... | ... | ... | ... | ... | ... | ... | ... | ... |
| 8966 | 60 | 140 | 69 | 60 | 64 | 140 | 171 | 174 |
| 8843 | 60 | 140 | 69 | 60 | 64 | 100 | 171 | 174 |
| 8734 | 140 | 140 | 69 | 60 | 64 | 60 | 171 | 174 |
| 8594 | 100 | 140 | 69 | 60 | 64 | 60 | 171 | 174 |
| 8179 | 60 | 140 | 69 | 60 | 64 | 60 | 171 | 174 |

Thrombin Generation in Actual Populations.

Thrombin generation using actual plasma factor composition data from an apparent healthy population (N=32), a severe hemophilia A population (N=16), and a warfarin treated group (N=65) was simulated and the 4 thrombin parameters extracted for each person in each group. The mean factor levels for each population are presented in Table 2.

TABLE 2

Factor levels for control, hemophilia & warfarin groups (Mean ± SD).

| Protein Factor | Control* (%) | Hemophilia# (%) | Warfarin$ (%) |
|---|---|---|---|
| VII | 108 ± 17 | 87 ± 29 | 30 ± 9 |
| X | 119 ± 21 | 110 ± 22 | 37 ± 10 |
| IX | 120 ± 20 | 107 ± 20 | 34 ± 7 |
| II | 111 ± 15 | 115 ± 15 | 29 ± 9 |
| VIII | 140 ± 27 | 0.4 ± 0.4 | 121 ± 29 |
| V | 109 ± 12 | 105 ± 20 | 105 ± 14 |
| TFPI | 114 ± 7 | 63 ± 12 | 111 ± 37 |
| AT | 100 ± 14 | 113 ± 11 | 104 ± 13 |

*Apparently healthy individuals (N = 32).
Severe hemophilia A individuals (N = 16), factor VIII levels ≤1% at the time of the blood draw.
$Warfarin treated individuals (N = 65, INR = 2.6 ± 0.4).

All factor levels in these populations are within their normal ranges, with the exception of fVIII in the hemophiliac population, and the vitamin K dependent proteins in the individuals undergoing warfarin therapy.

Thrombin Generation in a Hypothetical Abnormal Population.

To produce populations characterized by fIX deficiency, prothrombin deficiency and AT deficiency, the plasma composition data from the apparently healthy population (N=32) was altered as follows: each individual's fIX level set to 0.01% mean physiologic; or each individual's PT concentration set to 10% (severe PT deficiency) or 40% mean physiologic; or each individual's AT concentration set to 40% (heterozygous AT deficiency) mean physiologic. In each instance, all other factor concentrations were left at their individual measured values.

Model Sensitivity to Normal Range Variation in Factor Levels:

Analysis of Single Factor Dependence.

To characterize the impact of normal range variation in factor levels on model output of all species, all species with non zero values at time zero except Tf (8 independent species in total: II, V, VII/VIIa, VIII, IX, X, TFPI, AT) were altered, one at a time, in eleven evenly spaced intervals between the low normal and high normal value for that factor and time course profiles for all 34 species collected (2992 simulations). The clinically accepted normal range values were obtained from Fletcher Allen Health Care (Burlington, Vt.; see Table 3). For each of the 8 factors, the collection of cTGPs derived from the 11 initial factor concentrations for a given output species is referred to as the ensemble range for that species with respect to that factor (272 ensembles in total), with the profile reflecting all factors at one hundred percent their mean physiologic value defined as the standard profile for that species.

Ensemble Standard Deviation.

Figure 11A:
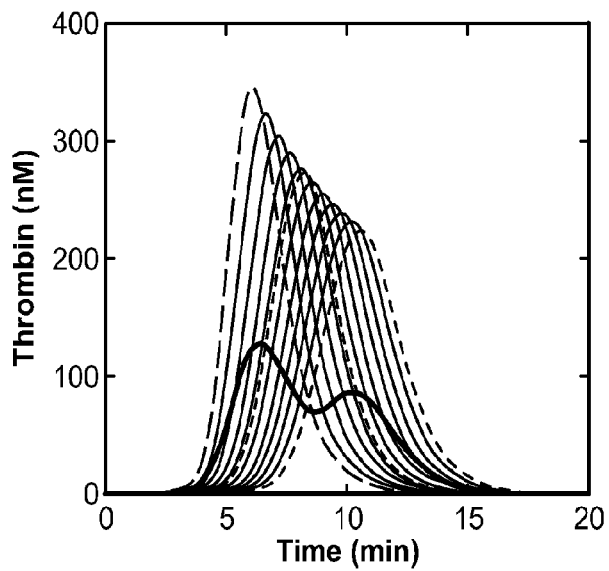
FIGS. 11 A-C are graphical views illustrating sensitivity of a model species (a-thrombin) to variation in initial factor concentration. Thrombin generation profiles resulting from varying in eleven intervals the initial concentrations of tissue factor pathway inhibitor (TFPI) (FIG. 11A: 46-171%) or AT (FIG. 11: 88-171%) across their normal range (Low: dotted, high: dash-dot, and 100%: dashed curves) are shown. The solid bold lines in these panels represent the ensemble standard deviation associated with the mean thrombin concentration at each time point.
FIG. 11C: The coefficient of variation (0) at each time point is plotted for TFPI and AT. The time averaged coefficient of variation values are shown in the parentheses and represent the mean of the coefficient of variation values across the 20-min simulation.
Figure 11B:
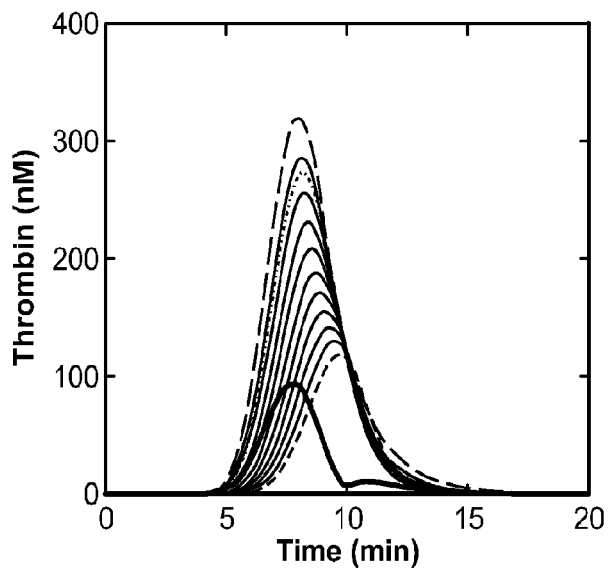

In order to evaluate the impact of normal range variation in each factor (g) on model output of each species, we utilized a modification of our previously described approach for analyzing our model's sensitivity to perturbations in its rate constants [(Danforth et al. 2009, infra]. For any given model output species (f) at any selected time (t) an ensemble standard deviation ($\sigma_g^{f(t)}$) can be calculated. It is designed to represent the variation in that species concentration at time t that occurs as a result of variation in the initial concentration of factor g when all other factors are held at their mean physiologic values. A group of predicted time courses (11 time courses) for species (f) generated by varying the initial concentration of factor g in linearly spaced intervals across its normal range provides the data set from which the ensemble standard deviation is calculated at 1 second intervals over the 1200 s time course see FIGS. 11A, B.

Coefficient of Variation.

The impact of variation in reaction concentration of the each of the 8 initially nonzero factors (g) on the production of any model species (f) was normalized using a coefficient of variation ($w_g^{f(t)}$) defined to be the ensemble standard deviation at each time t expressed a fraction of the peak value (P(f)) of that species when all factors are initially at 100% of their mean physiologic value (standard model curve). For example, thrombin (IIa) response to normal range variation in TFPI is given by $$w_{TFPI_{(t)}}^{IIa} = \frac{\sigma_{TFPI}^{IIa(t)}}{272\,nM},$$

where 272 nM thrombin is the peak concentration of thrombin under standard conditions. Normalization was performed in order to avoid numerical effects related to the differences in concentrations (>$10^6$) between species in the pathway. The peak concentration (P(f)) was chosen rather than the corresponding concentration at time t from the standard model curve or the ensemble mean curve because these are both time-dependent, see FIG. 11C.

Time Averaged Coefficients of Variation for Thrombin.

Figure 11C:
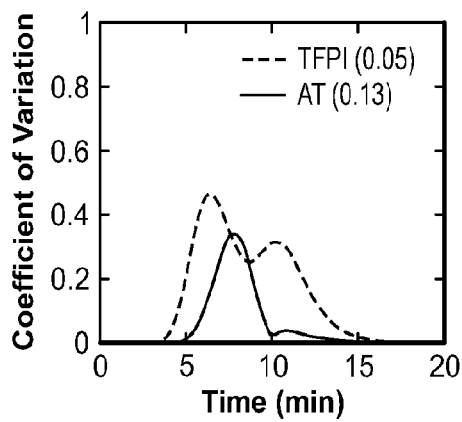
Figure 12A:
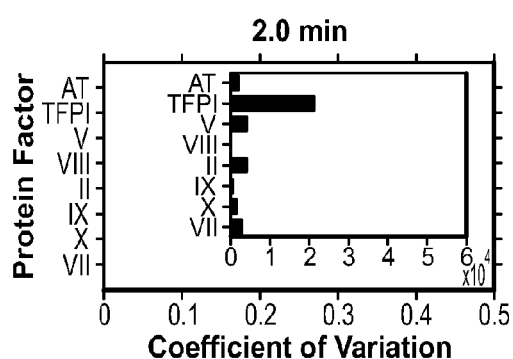
FIG. 12 are graphical views illustrating thrombin sensitivity across the normal range for each non-zero factor (g) at selected times. Coefficient of variation for thrombin ($w_g^{IIa}$ (t)) characterizing predicted thrombin concentrations is plotted for each of the 8 protein factors at reference times (FIG. 4) during the coagulation process. In panels representing 2.0 & 20.0 min, insets shows changes in the coefficient of variation that are dramatically smaller than other time points (10-x). Large bars imply that normal range variation leads to relatively higher variability in the level of thrombin at that time point.
Figure 12B:
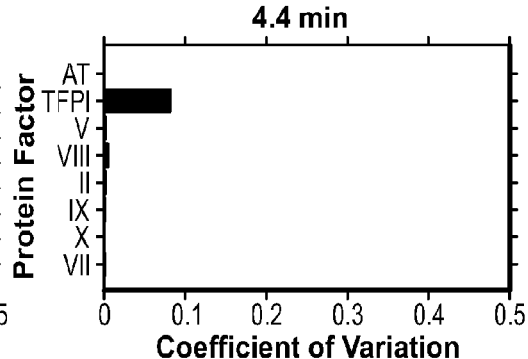
Figure 12C:
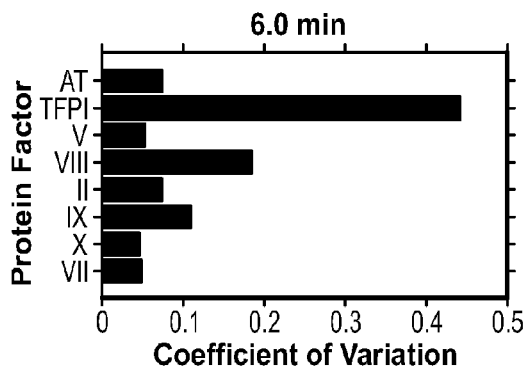
Figure 12D:
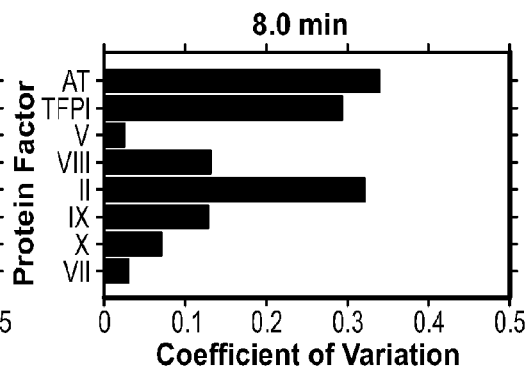
Figure 12E:
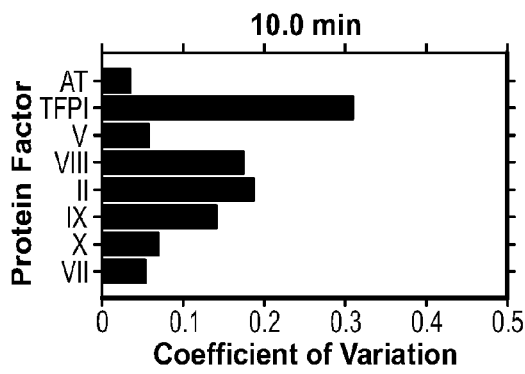
Figure 12F:
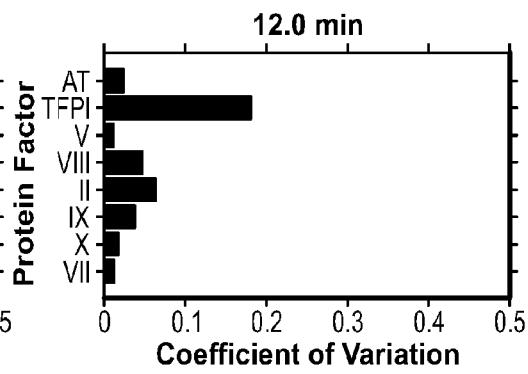
Figure 12G:
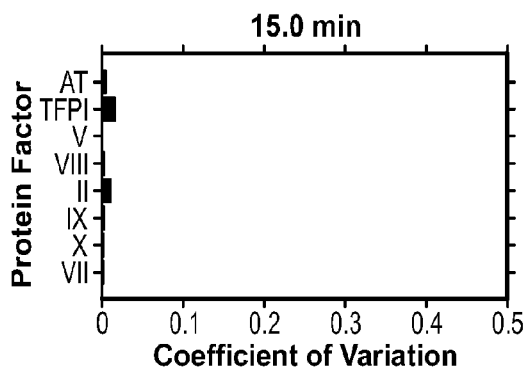
Figure 12H:
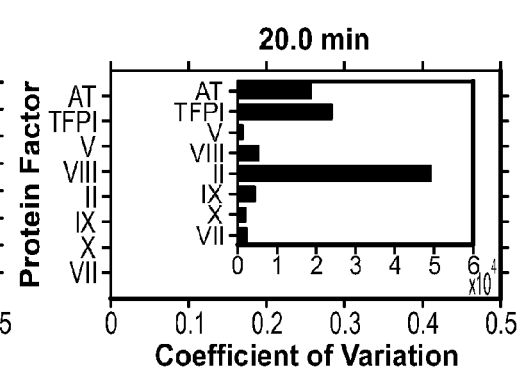
Figure 13A:
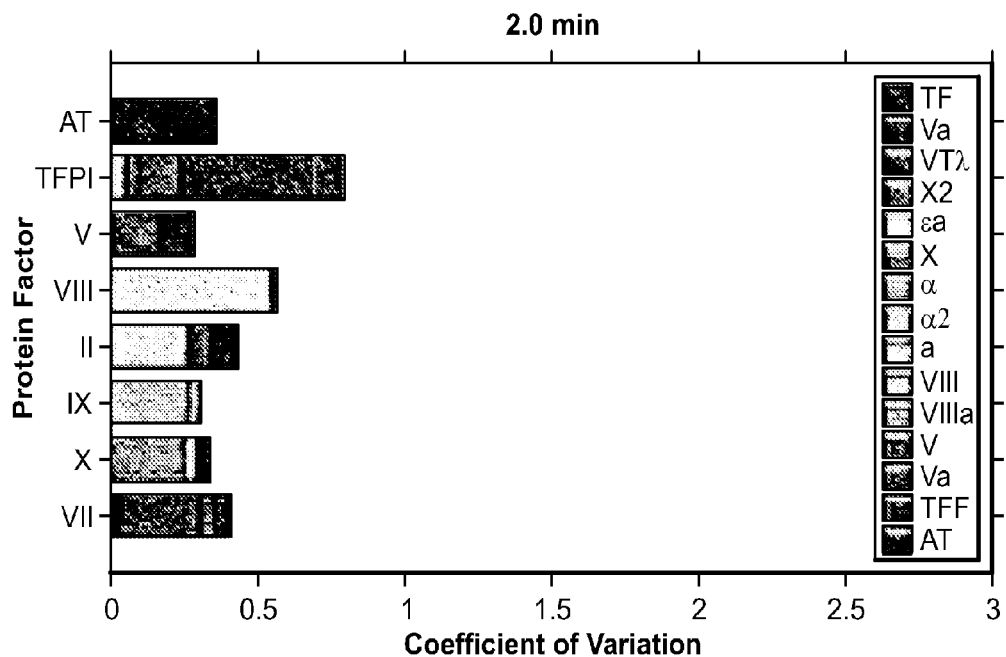
FIG. 13 are graphical views illustrating aggregate sensitivity of model species as a function of normal range variation of each factor (g) at selected times. Coefficients of variation for the 15 most sensitive model species for each of the 8 non-zero protein factors (g) at relevant times during the coagulation cascade are presented. Each species coefficient of variation is represented by a color and its magnitude by the length. Long bars imply the greatest effects of normal range variation on the dynamics of the simulation.
Figure 13B:
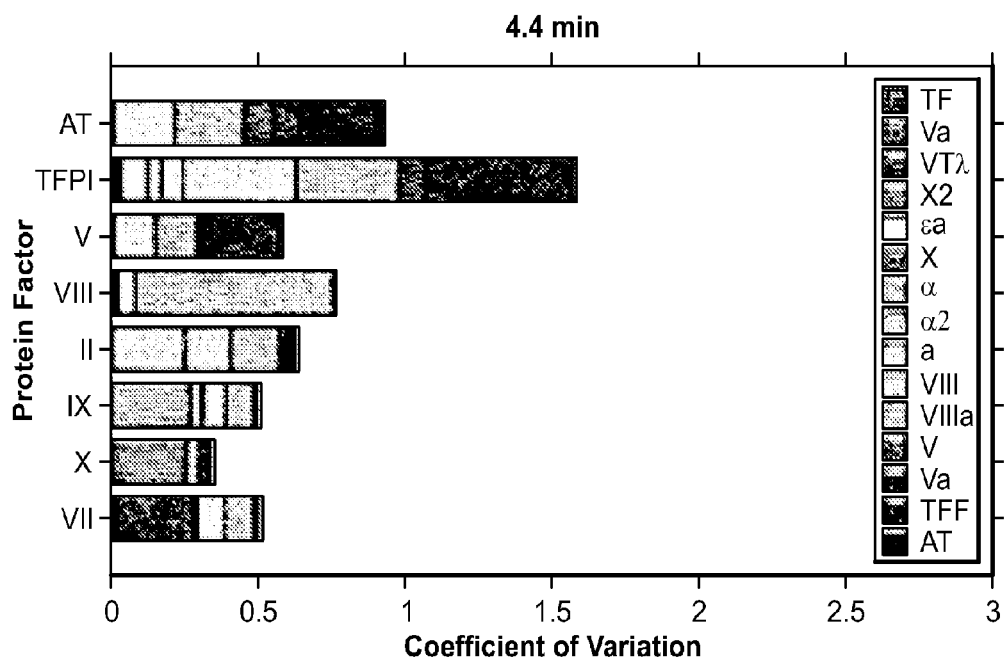
Figure 13C:
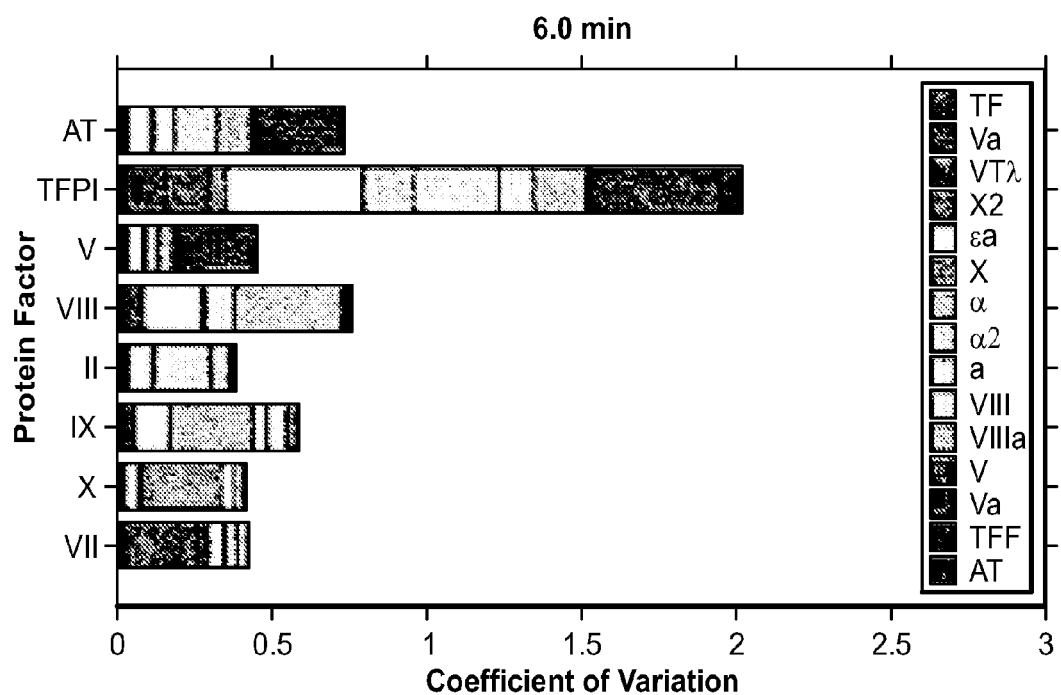
Figure 13D:
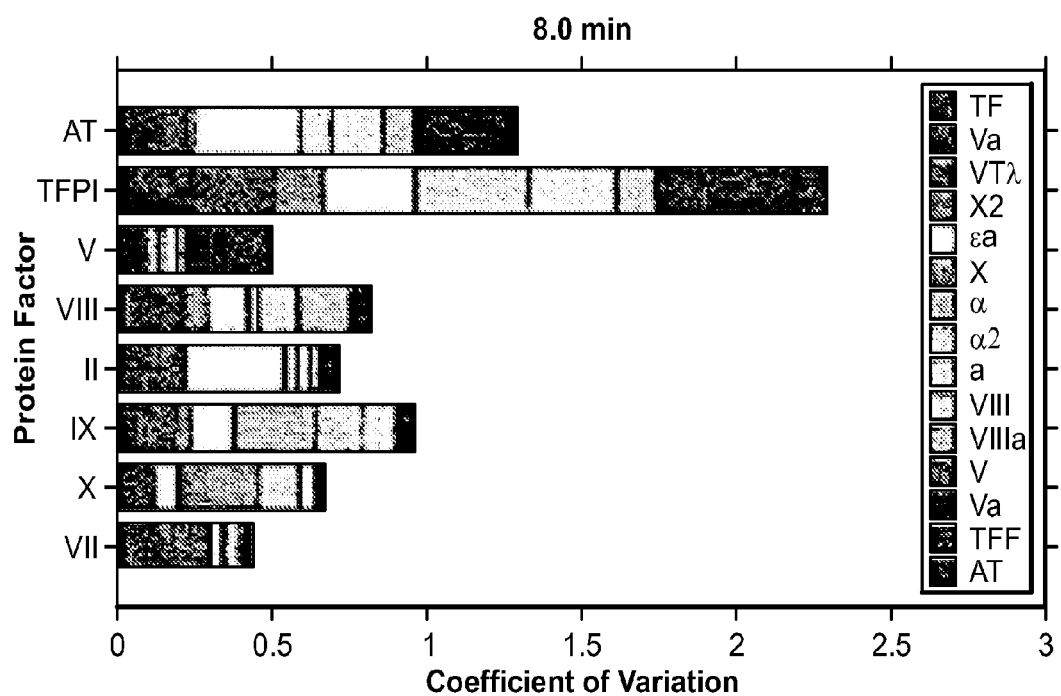
Figure 13E:
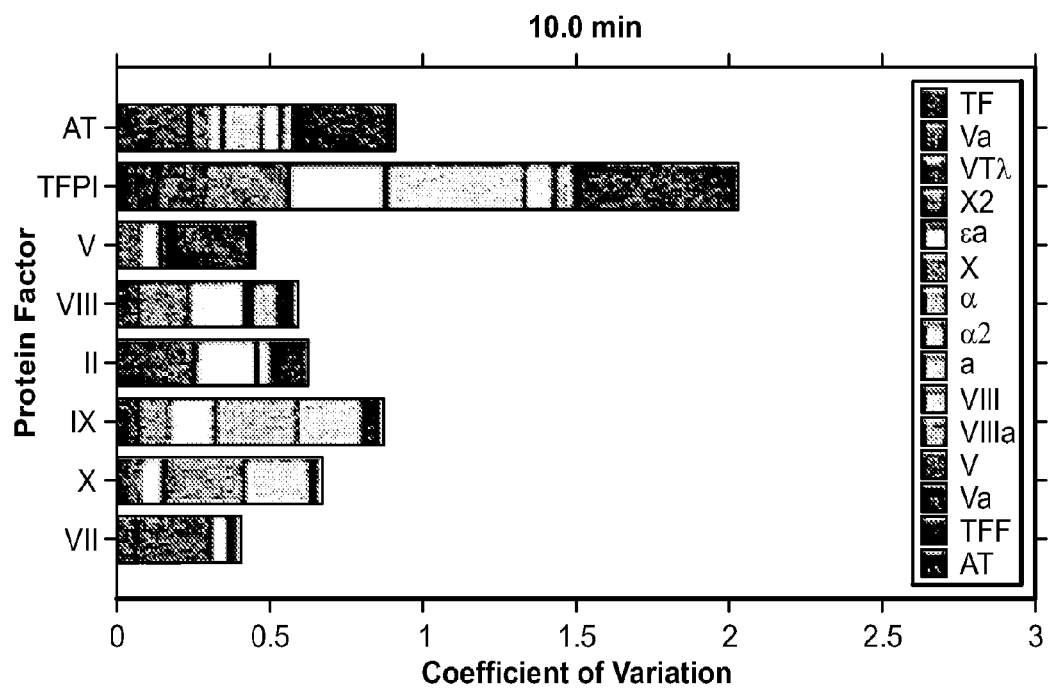
Figure 13F:
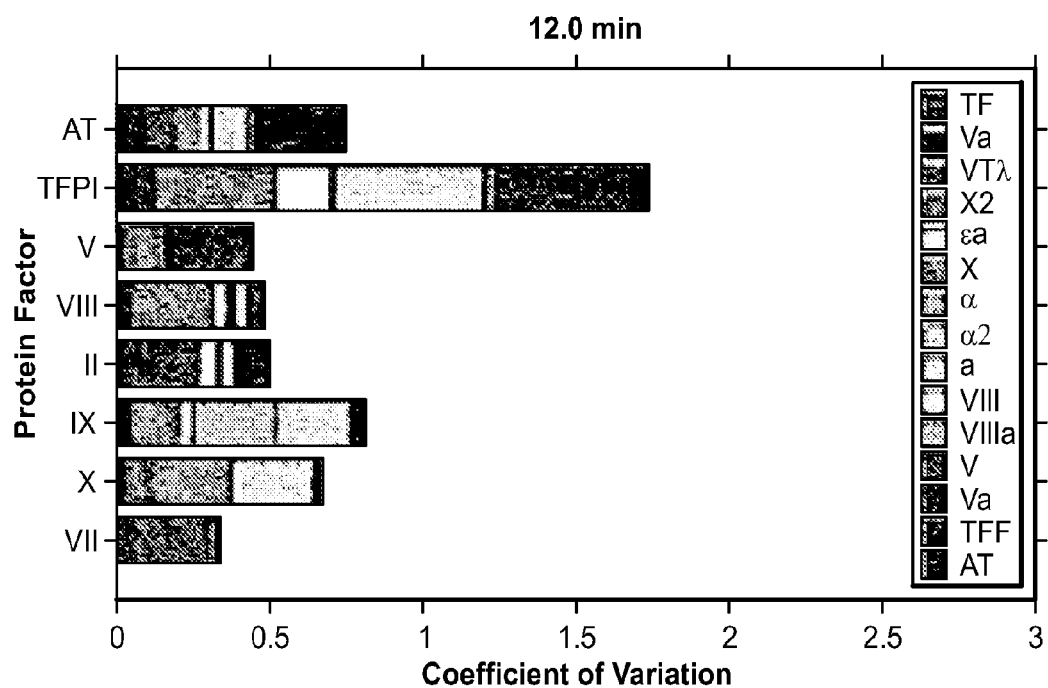
Figure 13G:
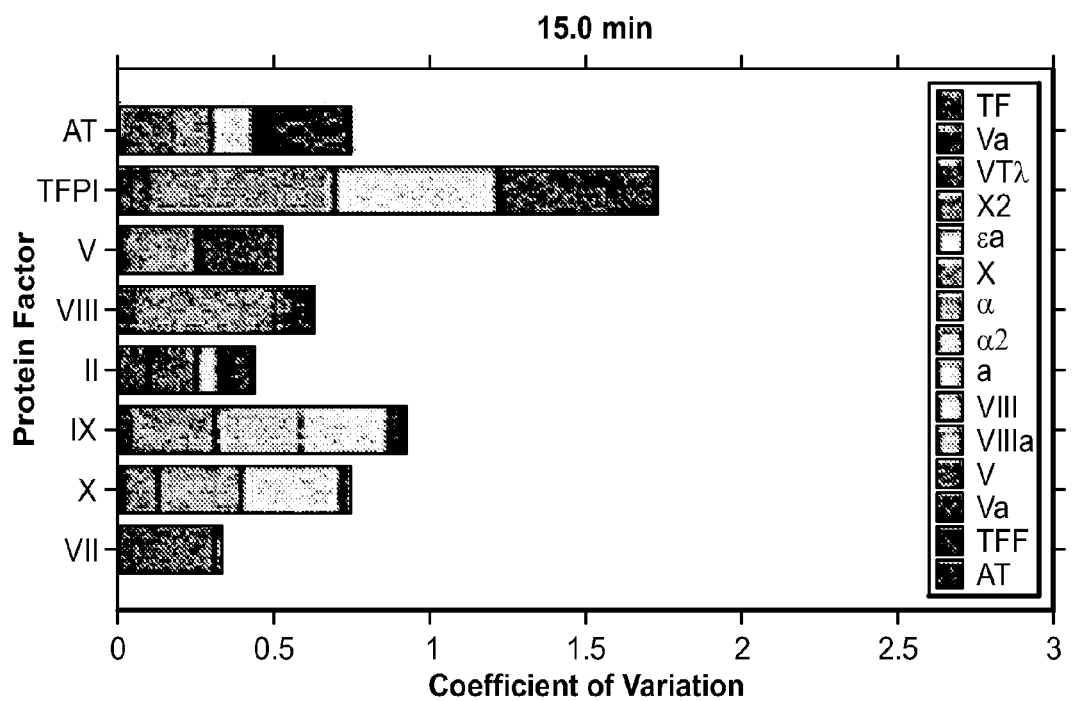
Figure 13H:
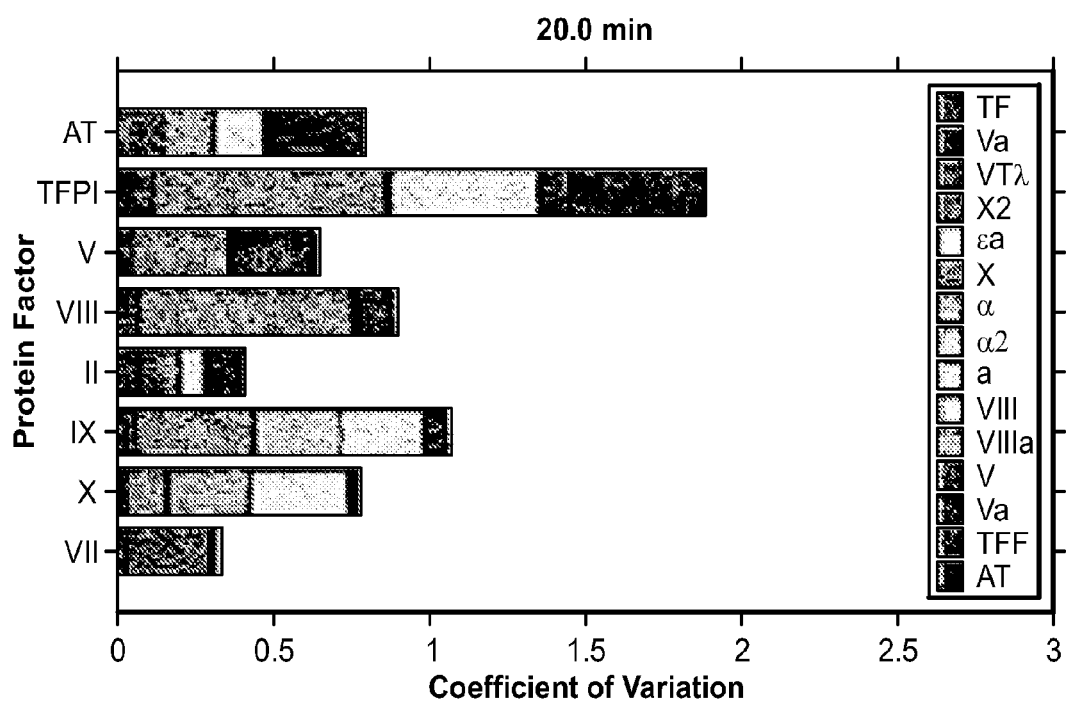

For each of the 8 non-zero initial factors (g), the coefficients of variation ($w_g^{IIa}(t)$) were averaged over the 1200 s time course to yield 8 time averaged coefficients of variation for thrombin (See FIG. 11C). These 8 values were summed, each individual value expressed as a fraction of that sum, and then ranked by the magnitude of its contribution to the total variation in thrombin induced by normal range variation of the 8 factors.

Time Averaged Coefficients of Variation for all Model Species.

For each non-zero factor (g) at time (t), the mean coefficient of variation for all resulting protein species is given by $\gamma_g(t) = 1/34 \sum_{f=1}^{34} w_g^f(t)$. The time average $\gamma_g(t)$ for factor (g) over the 20 minutes of the simulation is denoted by $\Gamma_g$. The 8 $\Gamma_g$ values were summed, each expressed as a fraction of the total, and then ranked by their magnitude (see, e.g., FIGS. 12 and 13).

Analysis of Pair Wise Variation in Factor Levels on Thrombin Generation.

Each pair of factors (28 possible) was varied together with the same 11 linearly spaced values within their individual normal ranges, leaving the other 6 factors at their mean physiologic value. This resulted in 121 cTGPs for each factor pair from which the four thrombin parameters were extracted. The range in each of the four parameters induced by variation in that factor pair was then identified and each of these range values expressed as a fraction of the largest perturbation in that parameter observed among the 28 factor pairs. For example coupled variations in AT and TFPI yielded the largest range in the time to 2 nM active thrombin values (3→8 min: 5 min) and thus all 27 other ranges for this thrombin parameter are ratioed to this range value.

The normal range variation in plasma concentration that characterizes the 8 model species with initial non-zero values is presented in Table 1. In order to assess the consequences of this variation, computationally derived thrombin generation profiles (cTGPs) were produced by assigning a specific normal range value to each of these factors and a constant concentration (5 pM) for tissue factor. In this analysis, the term "individual" refers to a unique ensemble of these 8 factors from which a cTGP, representing the model integrated effect of this ensemble, is generated. The ensemble having all factors at their mean physiologic level serves as a reference cTGP for assessing the relative intensity of thrombin generation characterizing other ensembles. To capture the maximum potential distribution (scope) of cTGPs resulting from normal range variation in these factors, a theoretical population of "normal" individuals, each with a unique ensemble of initial factor concentrations, was generated by allowing each factor to have 3 possible values spanning its normal range ($3^8$ or 6561 individuals). To quantify differences between these cTGPs, thrombin parameters were extracted from each cTGP (see FIG. 4).

Factor Composition and Thrombin Generation Phenotypes

Figure 5C:
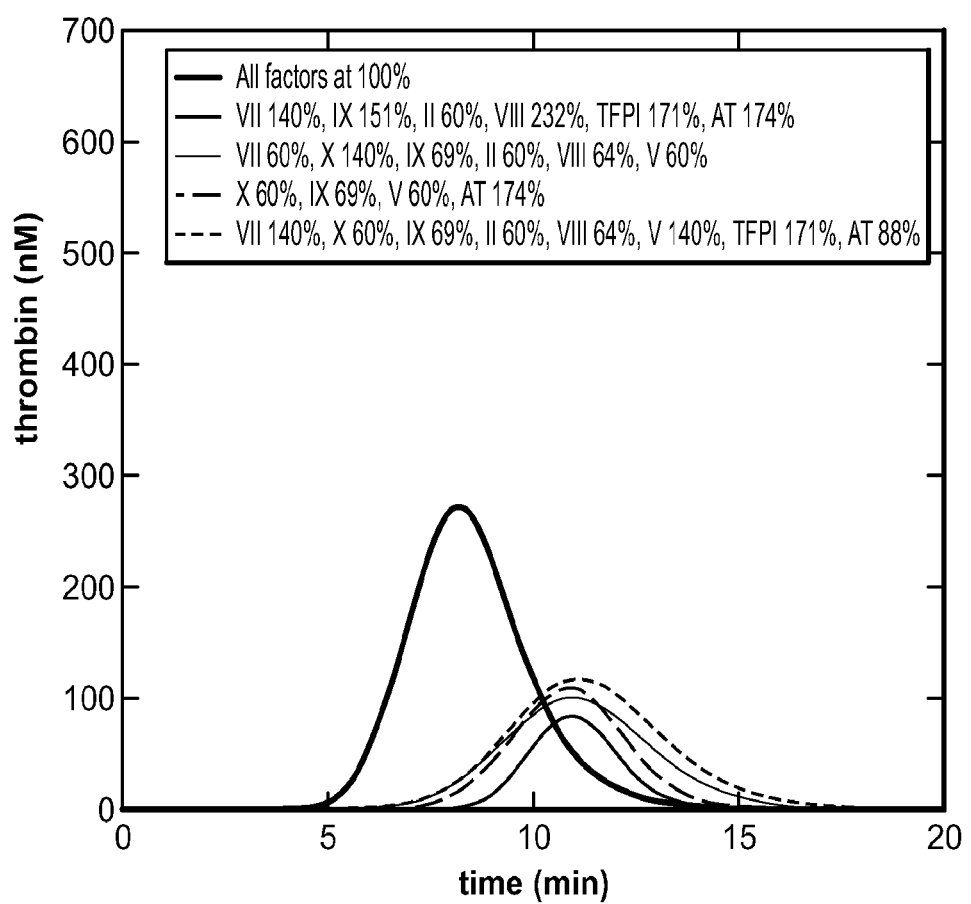

There is shown in FIGS. 5A-5C cTGPs of groups of individuals in the theoretical population selected because their cTGPs showed significant overlap despite their disparate factor composition. Factor ensembles (presented in the figure insets) with ~50% or greater differences in 4 to 8 factor concentrations characterize these individuals. Such individuals, representing disparate factor ensembles but with similar cTGPs, are defined to have the same thrombin generation phenotype. Thus three thrombin generation phenotypes are represented in FIGS. 5A-C.

In FIG. 5A, individuals with cTGPs that overlap the reference cTGP are shown. There is shown in FIG. 5B, C individuals with similarly disparate factor composition but overlapping cTGPs that display more or less robust thrombin generation respectively. In FIG. 5B, normal range factor variation produces ensembles resulting in cTGPs displaying a 2-3 fold shortening of the clot time parameter and 2 to 3 fold increases in the parameters max rate, max level and total thrombin compared to the reference cTGP. In FIG. 5C displays distinct ensembles that produce overlapping cTGPs characterized by a relatively attenuated response: a 2-3 fold prolongation of the clot time parameter and 2 to 3 fold decreases in the parameters max rate, max level and total thrombin compared to the reference cTGP.

The results of these limited comparisons highlight a consequence of normal range variation in factor levels on thrombin generation: factor variation per se (analyzing factor concentrations and not their integrated effect) is not a sufficient discriminator for predicting differences in thrombin generation between individuals. Ensembles, when integrated mechanistically, can effectively compensate for apparently procoagulant or anticoagulant variations in individual factor levels.

Thrombin parameters for the individual with all factors at mean physiologic values are: clot time—4.4 min; max rate—2.21 nM/s; max level—271.4 nM; and total thrombin—56458 nM●s.

TABLE 3

Typical initial coagulation factor concentrations and their normal ranges..

| Protein Factor | Variable | Initial Concentration (M) | Normal Range* (%) | LETS Population Range# (%) | In house Population (%) |
|---|---|---|---|---|---|
| TF | $x_1$ | $5 \times 10^{-12}$ | Undefined | Undefined | Undefined |
| VII | $x_2$ | $1 \times 10^{-8}$ | 60-140 | 41-171 | 76-147 |
| TF = VII | $x_3$ | 0 | | | |
| VIIa | $x_4$ | $1 \times 10^{-10}$ | 60-140 | | |
| TF = VIIa | $x_5$ | 0 | | | |
| Xa | $x_6$ | 0 | | | |
| IIa | $x_7$ | 0 | | | |
| X | $x_8$ | $1.6 \times 10^{-7}$ | 60-140 | 46-163 | 83-184 |
| TF = VIIa = X | $x_9$ | 0 | | | |
| TF = VIIa = Xa | $x_{10}$ | 0 | | | |
| IX | $x_{11}$ | $9 \times 10^{-8}$ | 69-151 | 52-188 | 74-151 |
| TF = VIIa = IX | $x_{12}$ | 0 | | | |
| IXa | $x_{13}$ | 0 | | | |
| II | $x_{14}$ | $1.4 \times 10^{-6}$ | 60-140 | 55-153 | 89-152 |
| VIII | $x_{15}$ | $7 \times 10^{-10}$ | 64-232 | 49-232 | 99-193 |
| VIIIa | $x_{16}$ | 0 | | | |
| IXa = VIIa | $x_{17}$ | 0 | | | |
| IXa = VIIIa = X | $x_{18}$ | 0 | | | |
| VIII.1ca1 | $x_{19}$ | 0 | | | |
| VIII.a2 | $x_{20}$ | 0 | | | |
| V | $x_{21}$ | $2 \times 10^{-8}$ | 60-140 | 47-302 | 86-138 |
| Va | $x_{22}$ | 0 | | | |
| Xa = Va | $x_{23}$ | 0 | | | |
| Xa = Va = II | $x_{24}$ | 0 | | | |
| mIIa | $x_{25}$ | 0 | | | |
| TFPI | $x_{26}$ | $2.5 \times 10^{-9}$ | 46-171 | 46-170 | 88-148 |
| Xa = TFPI | $x_{27}$ | 0 | | | |
| TF = VIIa = Xa = TFPI | $x_{28}$ | 0 | | | |
| AT | $x_{29}$ | $3.4 \times 10^{-6}$ | 88-174 | 63-125 | 74-131 |
| Xa = AT | $x_{30}$ | 0 | | | |
| mIIa = AT | $x_{31}$ | 0 | | | |
| IXa = AT | $x_{32}$ | 0 | | | |
| IIa = At | $x_{33}$ | 0 | | | |
| TF = VIIa = AT | $x_{34}$ | 0 | | | |

*The normal ranges (Reference Intervals) were determined in 2006/2007 by The Fletcher Allen Health Care Special Coagulation/Hematology Laboratory (FAHC, Burlington, Vermont). They tested equal numbers of normal males and females (n = 75 plasmas/gender) with 50 donors supplied from Precision Biologic and 25 donors drawn at FAHC. The reference ranges were calculated using the mean +/− 2SD.
van der Meer et al (1997) Thromb Haemost 78: 631-5.

The Possible Range of "Normal" Thrombin Generation Phenotypes

Figure 6:
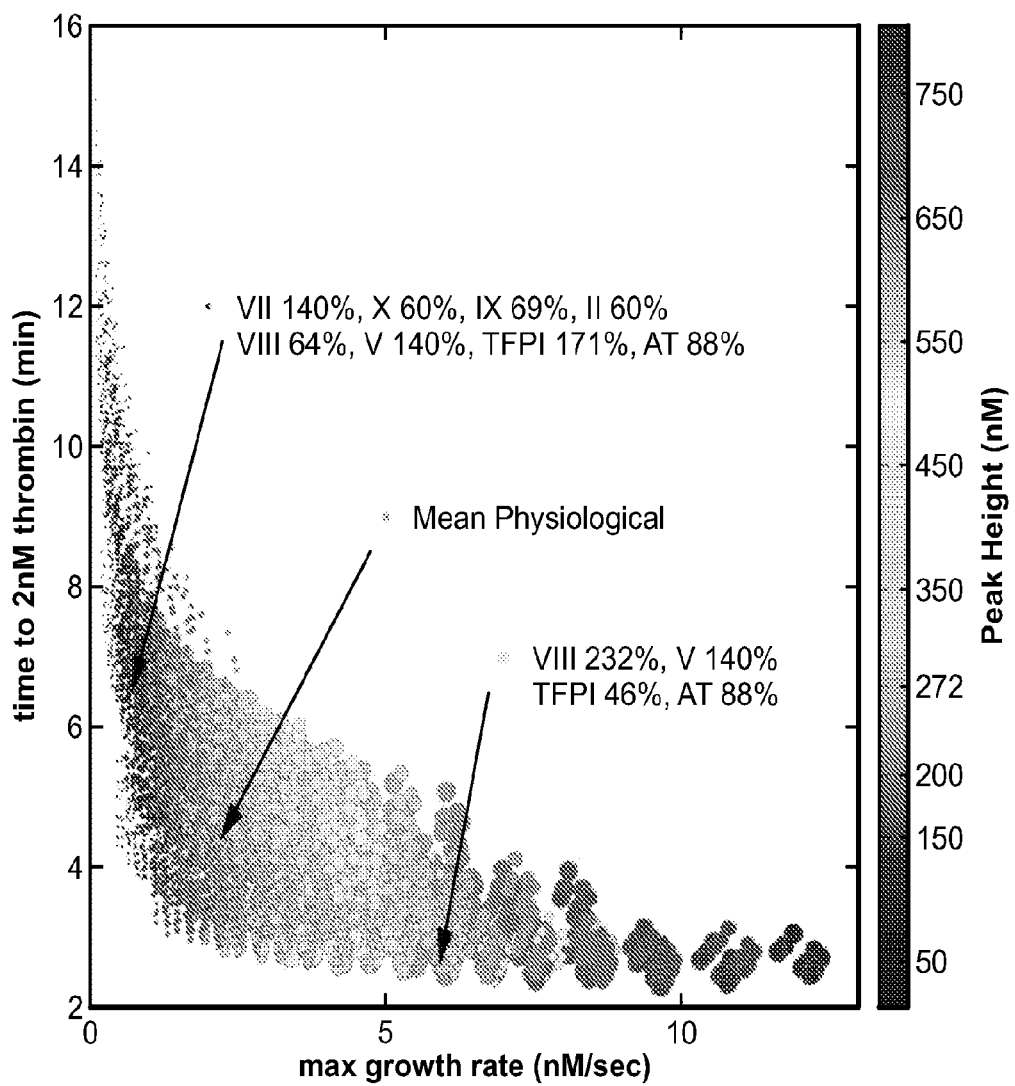
FIG. 6 is a graphical view of thrombin generation phenotypes in an hypothetical population defined by normal range variation in factor levels. Each individual in the population (6561) is defined by 4 thrombin parameters and their phenotype represented graphically by a positioned colored circle: y axis—time to 2 nM thrombin, range (2.3→15 min); x axis—maximum rate of thrombin generation, range (0.1→12.4 nM/s); color—maximum thrombin level, range (23●→792 nM●); and size—total thrombin, range (8,179→134,340 sec*nM○). Inset: An individual with all factors at their mean physiologic value is depicted, the arrow indicating that individual's position in the population. Similarly, representative individuals from FIGS. 5B and C are included.

FIG. 6 compares all individuals in the theoretical population in terms of their relative ability to generate thrombin by creating a graphic representation of each individual that reflects the magnitude their thrombin parameters. Individuals (model integrated factor ensembles) are depicted by a positioned, colored ball of specific size, a collective representation of the 4 thrombin parameters extracted from their respective cTGPs. Time to clot (y axis) and max rate parameters (x axis) position each individual, while color indicates the max level and size defines the total thrombin parameter. To relate the differences between cTGPs observed in FIGS. 5A-C to this form of presentation, 3 individuals are highlighted: an individual with all factors at mean physiologic concentrations and individuals from FIGS. 5A, B. The levels of variation for the thrombin parameters in this population are as follows: 6.5 fold for the clot time (2.3 to 14.97 min); 33.4 fold for max level (23.7 to 792.4 nM); 120 fold for max rate (0.1 to 12.4 nM/s); and 17 fold for total thrombin (8179 to 134338 nM s) (see Table 3).

This population is designed to set the outer boundaries for the types of thrombin generation phenotypes possible because of normal range variations in coagulation factor levels. As is evident from FIGS. 5A-C and visual inspection of FIG. 6, significant overlap of individuals occurs, and thus the number of thrombin generation phenotypes is less than the number of individuals (factor ensembles). The question that presents itself is whether all potential phenotypes derived from ensembles with normal factor levels are representative of a normal or healthy hemostatic response?

Normal Thrombin Generation Phenotypes; Possible Range Vs Actual

Computationally analyzed thrombin generation using factor composition data from an apparently healthy control group of 473 individuals from the Leidin Thrombophilia Study has been reported (Brummel-Ziedins et al. (2005) J Thromb Haemost 3: 1472-1481). Factor level variation in this population was similar to or exceeded the ranges used to generate the theoretical population presented in FIG. 6 (see also Table 1). In this population of Dutch individuals (272 women, 201 men) the range in thrombin parameters was: 3.3 fold for the clot time; 3.9 fold for maximum level thrombin; 4.8 fold for maximum rate; and 4.5 fold for total thrombin. The 2 to 20 fold larger ranges predicted for the thrombin parameters of the theoretical population reflect factor ensembles that were possible in the LETS population (given the factor composition ranges) but that did not occur.

The wider ranges of thrombin parameters characterizing the theoretical population have two potential origins: a methodological one due to its larger size, emphasis on the extremes of each factor range and its treatment of all possible ensembles as of equal probability; or a biological one reflecting the fact that some ensembles, perhaps those resulting in individuals with the more extreme characteristics in FIG. 6, are consistent with coagulopathic states and thus would not be found in a healthy population.

Relevant coagulation factor composition data from comparably sized populations of apparently healthy individuals are not available currently. However, factor composition data for smaller populations, including those with coagulopathies resulting from inherited or pharmacologically induced deficiency states, are available. A comparative analysis of individuals with defined, composition-based hemostatic defects resulting in a diminished coagulant response was performed to determine whether their thrombin generation phenotypes fall within the theoretical normal range population distribution.

Figure 7:
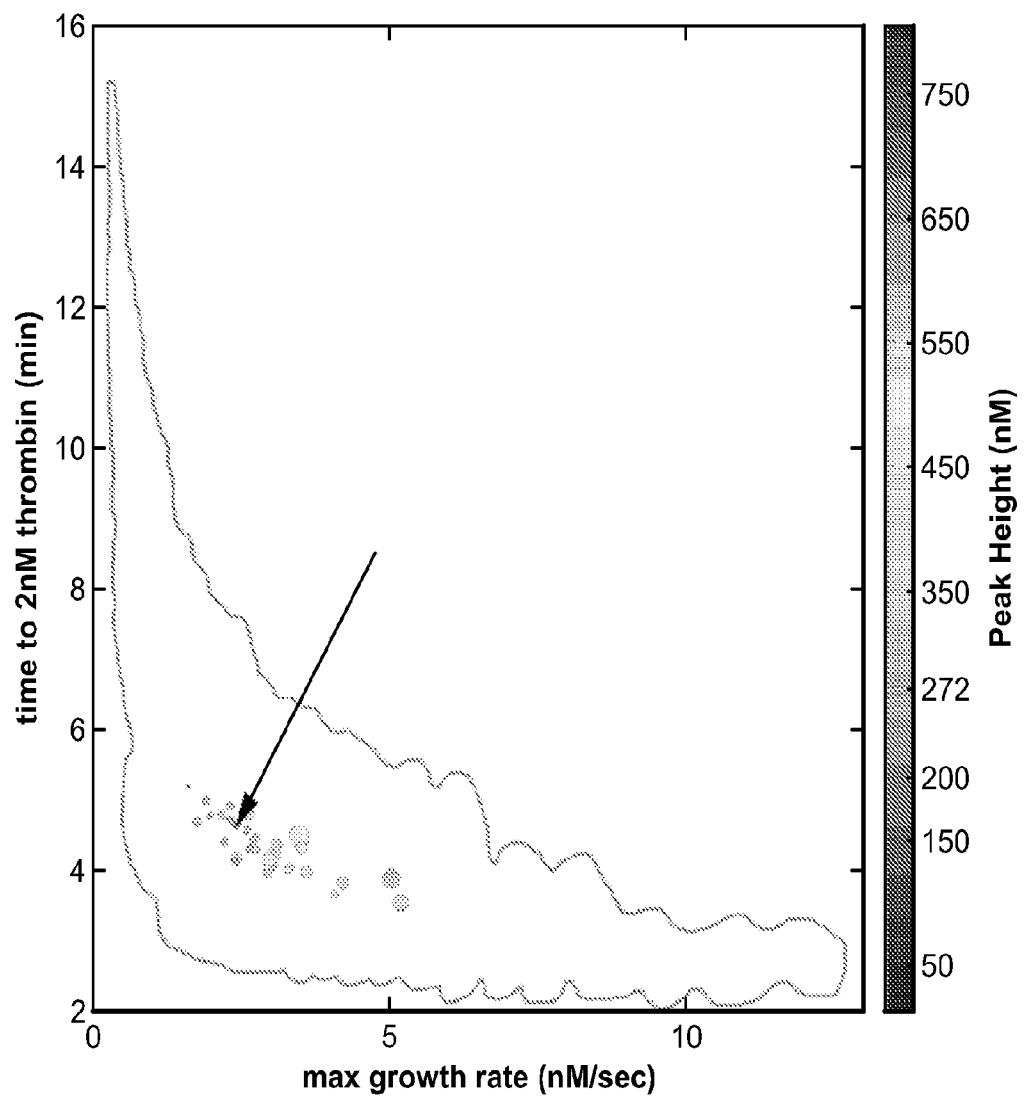
FIG. 7 is a graphical view of thrombin generation phenotypes in a population of apparently healthy individuals. Plasma factor composition for 32 individuals was used to generate time courses of thrombin generation, thrombin parameters were extracted and each individual represented as shown in FIG. 6 (see also brief description of FIG. 6 above). The boundaries (magenta) of the hypothetical population are outlined and an individual with all factors at their mean physiologic values is also presented.

There is shown in FIG. 7, a graphic representation of the thrombin parameters characterizing a population of apparently healthy individuals (N=32), with the boundary of the theoretical population (from FIG. 6) also shown. Factor level variation in this population is presented in Table 1 and the mean factor levels in Table 2. The max level and max rate parameters vary ~3 fold in this population, the total thrombin parameter 4 fold and the clot time parameter 1.4 fold. The parameter ranges for max level, max rate and total thrombin are similar to those reported for the larger LETS population (N=473) while the range of clot time values in this population is ~40% that of LETS. Thus both populations appear confined to a relatively small region of the potential distribution of thrombin generation phenotypes available because of normal range variation in coagulation factor levels.

Figure 8A:
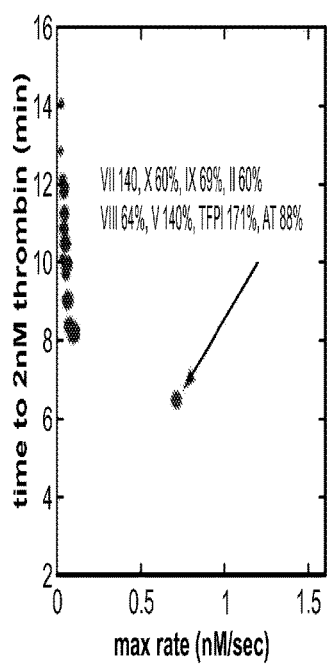
FIGS. 8A-C are graphical views of thrombin generation phenotypes in hemophilia A individuals and individuals undergoing warfarin therapy. Plasma factor composition was used to generate time courses of thrombin generation, thrombin parameters extracted and each individual represented in the same manner as FIG. 6 (see also brief description of FIG. 6 above). The x axis (max rate) is truncated (0-1.2 nM/s) and the size of each individual symbol (total thrombin parameter) has been increased by a factor of 5 relative to FIG. 6 to improve visibility. Also indicated (arrow) is an individual shown in FIG. 5C and FIG. 6. FIG.
Figure 8B:
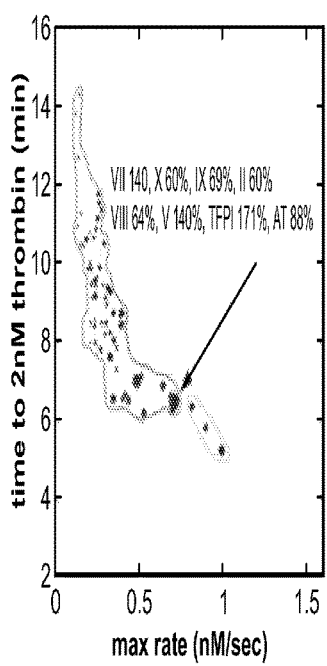
Figure 8C:
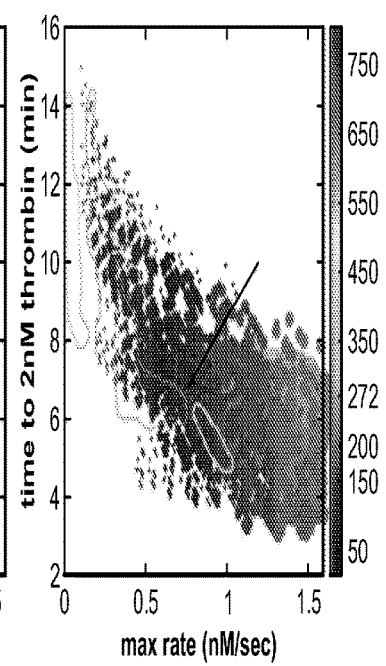

There is shown in FIGS. 8A-C a comparison of thrombin generation between a group of severe hemophilia A individuals (N=16; factor VIII<1%; FIG. 8A), a cohort of individuals anticoagulated with warfarin (N=65; FIG. 8B) and the relevant subset of the theoretical population (FIG. 8C). Plasma composition data for the hemophilia and warfarin treated populations are presented in Table 2. To facilitate the comparison, the max rate (x axis) parameter extends only to 1.2 nM/s and the size of each individual's symbol (total thrombin parameter) has been increased by a factor of 5 relative to FIG. 6 to improve its visibility. The boundaries for the hemophilia and warfarin-treated groups are indicated in panel C.

In general, individuals with severe hemophilia A, in the absence of replacement therapy with rFVIII or other agents, experience prolonged and potentially life threatening bleeding in response to a hemostatic challenge as well as episodes of "spontaneous bleeding". In this hemophilia population, all factors other than fVIII are within the normal range (See Table 2). FVIII concentrations vary from 0.07% to 1% mean physiologic. For the overall population the parameter ranges were: time to 2 nM thrombin—y axis, range (8.2→14 min); maximum rate of thrombin generation—x axis, range (0.02→097 nM/s); maximum thrombin level—color, range (16→50 nM); and total thrombin—size, range (17300→40845 nM●s).

As can be seen by comparing the distribution of phenotypes in FIG. 8C with that of FIG. 8A, the hemophilia population is positioned outside the most extreme phenotypes in the hypothetical normal population. These individuals are characterized by lower max rates but substantially higher total thrombin values across their distribution than their nearest neighbors in the hypothetical population. The defect in thrombin generation occasioned by severe FVIII deficiency also segregates these individuals from the warfarin-treated group, again drive by differences in max rate and total thrombin parameters.

The warfarin treated individuals represented in FIG. 8B, were initially considered, in terms of their clinical history, to be stably anticoagulated, as assessed by a 2 to 3 fold prolongation of their plasma clotting time in a standardized assay (INR: 2 to 3.3). In this population, the non vitamin K dependent (VKD) protein concentrations are all within the normal range, while the vitamin K dependent proteins (fII, fX, fIX, fVII/fVIIa) are suppressed 50 to 90%, with the level of suppression of each VKD protein varying between individuals. For the overall population the parameter ranges were: time to 2 nM thrombin, range (5.3→17 min); maximum rate of thrombin generation, range (0.08→1 nM/s); maximum thrombin level, range (13→100 nM); and total thrombin, range (6048→18978 nM●s).

The 65 individuals of the warfarin-treated population distribute within the region of the hypothetical population characterized by low max rates and prolonged clot times (see FIG. 8A) This is demonstrated more clearly in FIG. 8C, where the boundaries of the warfarin treated population are indicated by the orange line. Their overall characteristics, i.e. their 4 thrombin parameters, do not distinguish them from their nearest neighbors in the hypothetical population, suggesting that this region of the theoretical population is characterized by thrombin generation phenotypes reflecting a compromised coagulant response.

Three of the warfarin-treated individuals (circled in FIG. 8B) were subsequently reported to have suffered a thrombotic event. The graphical method employed separates these individuals from the remainder of the warfarin-treated group, primarily because of their max rate parameter, consistent with the idea that they were under anticoagulated despite clinical INR values between 2.1 and 2.5. Inspection of their plasma factor composition data shows no obvious differences between their VKD protein levels and the overall population; however, within the group of non VKD proteins, their TFPI values are at the low end of the range characterizing this population while their fVIII values are at the high end (see Table 2. These compositional data are consistent with the graphical characterization of these individuals as being under anticoagulated compared to the whole group in two ways: the pattern of high fVIII and low TFPI levels is computationally consistent with more robust thrombin generation; and the prothrombin time assay, which is the basis for INR metric, is relatively insensitive to variations in TFPI and FVIII levels and thus would not identify these individuals as insufficiently anticoagulated.

To further test the "normalcy" of this hypothetical population of thrombin phenotypes, additional populations representing "bleeding" phenotypes (fIX deficiency, prothrombin deficiency) or prothrombotic phenotypes (antithrombin deficiency) were analyzed. These populations were generated using the group (N=32) of apparently healthy individuals for which factor composition data was available (see Tables 2 and 3). In each case, all factors were left at their individual specific values except fIX or prothrombin or antithrombin, which were set to an average value characterizing their clinical deficiency state.

Figure 9A:
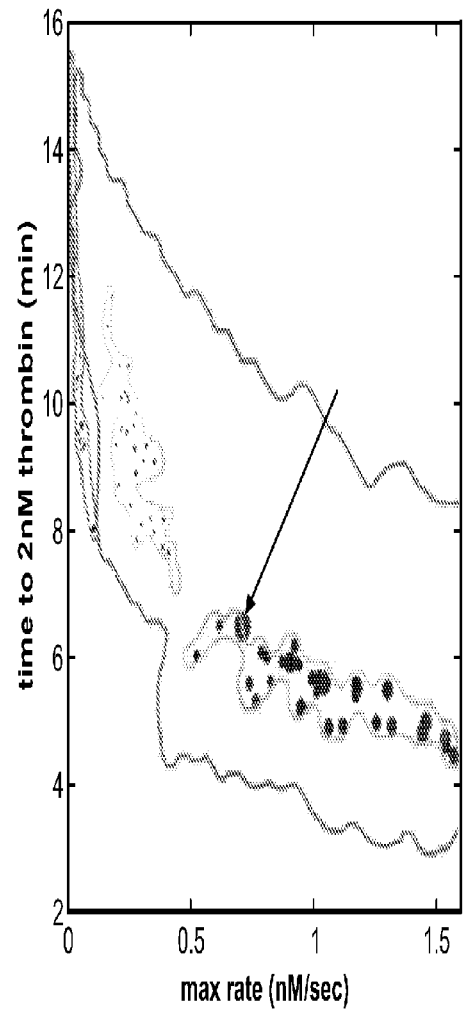
FIGS. 9A, B are graphical views that visualize thrombin generation phenotypes for hypothetical fIX deficiency, fII deficiency and AT deficiency. Plasma factor composition for each of 32 apparently healthy individuals was altered in one factor to reflect each deficiency state, time courses of thrombin generation analyzed for thrombin parameters and each individual represented as described in the FIG. 6 legend. There is shown in FIG. 9A, severe fIX deficiency (fIX=0.01% mean physiologic); severe fII deficiency (fII-10% mean physiologic); heterozygous fII deficiency (fII=40% mean physiologic). The x axis (max rate) is truncated (0-1.2 nM/s) and the size of each individual symbol (total thrombin parameter) has been increased by a factor of 5 relative to FIG. 6 to improve visibility. Also included is the reference individual from Figure EC-4. There is shown in FIG. 9B, heterozygous AT deficiency (AT=40% mean physiologic). Note that x axis shows the full range depicted in FIGS. 6 and 7. An individual with all factors at mean physiologic is shown along with an individual in FIG. 5B and FIG. 6. The boundaries of the hypothetical population are also shown in FIGS. 9A, B.

There is shown in FIG. 9A, the distributions of the individuals in the artificial fIX and prothrombin deficient groups. The outer boundaries of the theoretical population are depicted by the yellow line, with each group representing a one factor deficiency state circumscribed to define its limits. The size of each individual's symbol (total thrombin parameter) has been increased by a factor of five to improve its visibility and the x axis is truncated.

The fIX deficient population was modeled to represent a severe deficiency state, with fXI levels set to 0.01%. In general the bleeding problems associated with severe fIX deficiency (fIX<1%) are similar to those characterizing hemophilia A. The distribution of this artificial hemophilia B population lies outside the hypothetical population and appears roughly equivalent to the one characterizing actual hemophilia individuals (FIG. 8A). Differences in the total thrombin parameter between the actual hemophilia A individuals (FIG. 8A) and the artificial fiX deficient individuals reflect the fact that most of the hemophilia A individuals have higher fVIII levels than the fiX levels selected for "hemophilia B" population.

Two levels of prothrombin deficiency are also represented in FIG. 9A, with the prothrombin concentration set to 10% or 40% of its mean physiologic value in each of the 32 control individuals. Clinically, prothrombin deficiency is a rare coagulation disorder with homozygous individuals displaying prothrombin levels less than 10% mean physiologic; it is characterized by severe, often life threatening bleeding episodes (Lancellotti et al. (2009) Semin Thromb Hemost 35: 367-381). Heterozygous individuals with prothrombin levels 40 to 60% mean physiologic are usually asymptomatic, with excess bleeding occurring occasionally after surgical procedures.

The model representation of homozygous prothrombin deficiency (FIG. 9A) places these individuals along the edge of the theoretical population, overlapping, with respect to three of the thrombin parameters, the more highly anticoagulated individuals in the warfarin population (FIG. 8B). However, the total thrombin parameter for individuals with this level of PT deficiency is suppressed relative to the total thrombin values typifying the nearest neighbors in the theoretical population and the warfarin-treated population. The distinction between stably anticoagulated individuals on warfarin and severe prothrombin deficiency is consistent with the more extreme hemorrhagic phenotype seen in severe prothrombin deficiency.

In contrast, thrombin parameter analysis of individuals modeled to be heterozygous in their prothrombin deficiency (40% mean physiologic) indicates that this population is embedded within the boundaries of the hypothetical population. Neither max level or total thrombin parameters distinguishes these individuals from their nearest neighbor in the theoretical population. If one excludes the three warfarin-treated individuals who proved to be insufficiently anticoagulated, these individuals are situated outside the warfarin-treated population, displaying shorter clot times and larger max rates, parameter differences consistent with their overall lack of bleeding incidents, Heterozygous AT deficiency, with an incidence rate of 1 to 500 to 1 to 5000 in the general population, is characterized by AT concentrations 40 to 60% mean physiologic, below the normal range variation of ~80 to 170% mean physiologic—see Table 1 (Patnaik et al. (2008) Haemophilia 14: 1229-1239). These lower levels of AT induce a prothrombotic phenotype associated with a 5 to 50 fold increased risk for venous embolism.

Figure 9B:
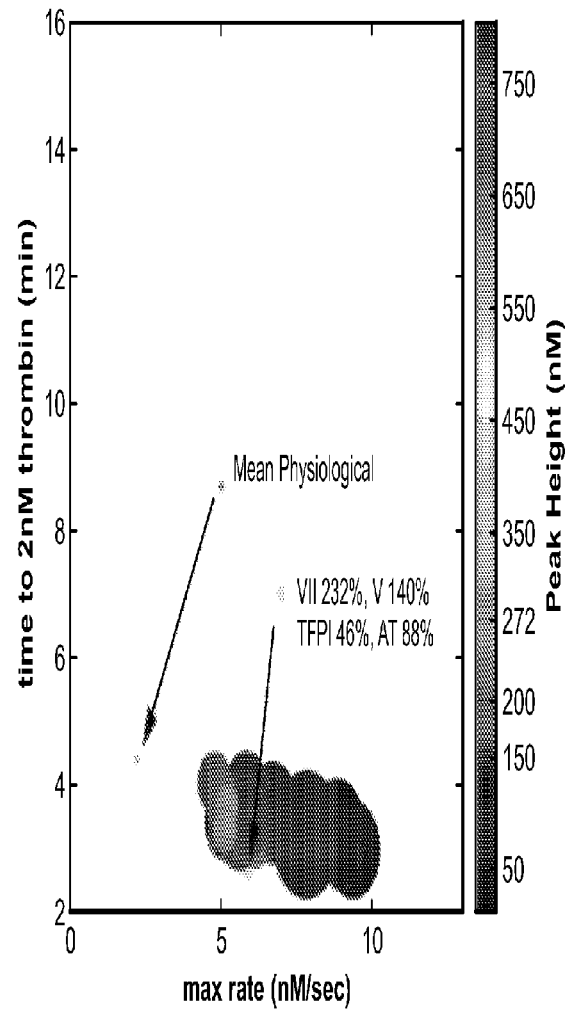
Figure 10A:
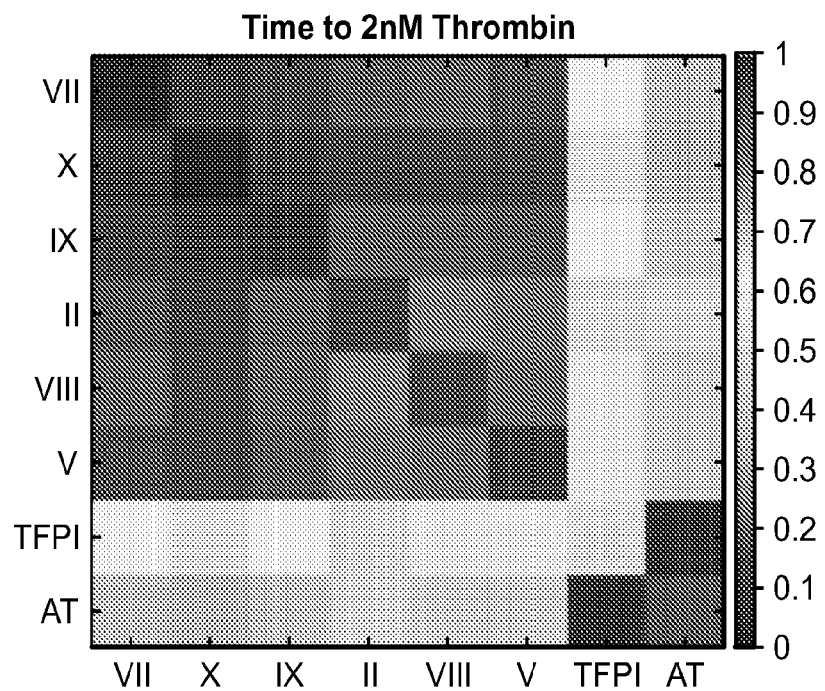
FIGS. 10A-10D provides illustrative views of factor pair induced variation in thrombin parameters. Pairs of factors (28 possible) were varied through their normal range, thrombin parameters were extracted from resulting computational thrombin generation profiles, the factor pair induced ranges for each thrombin parameter established, and then the set of 28 ranges for each thrombin parameter expressed as a function of the largest induced range for that parameter. The color scale reflects the normalized range values. Each parameter box (64 normalized range values) shows the 28 factor pair effects (in duplicate) and the relative intensity of each single factor (8 total) contribution to variation in the indicated thrombin parameter (see reverse diagonal: bottom right to upper left).
Figure 10B:
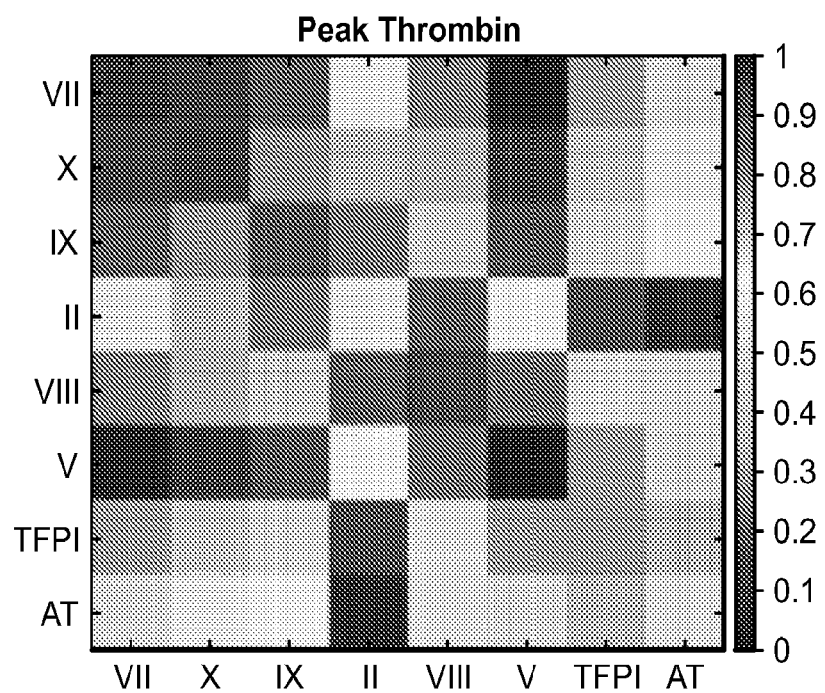
Figure 10C:
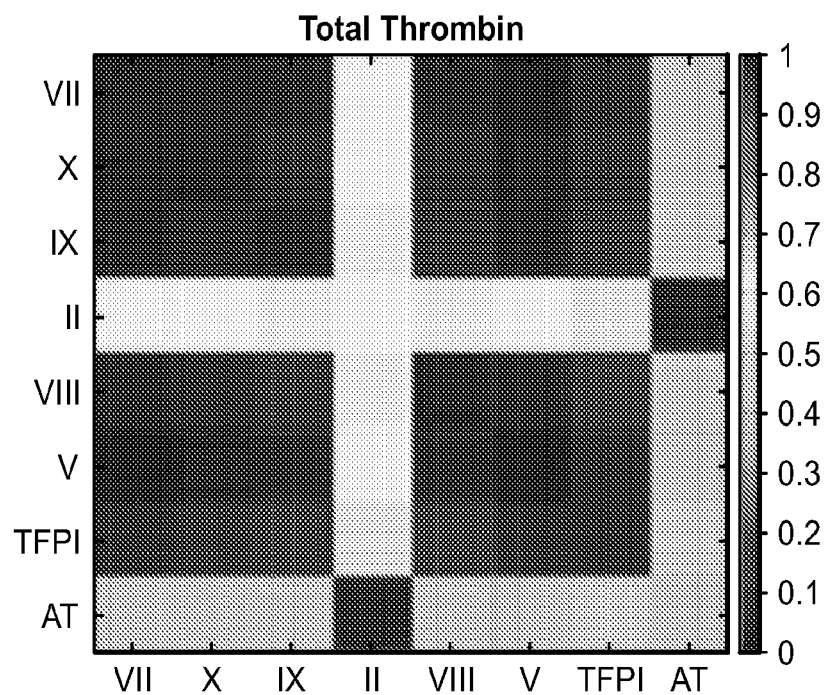
Figure 10D:
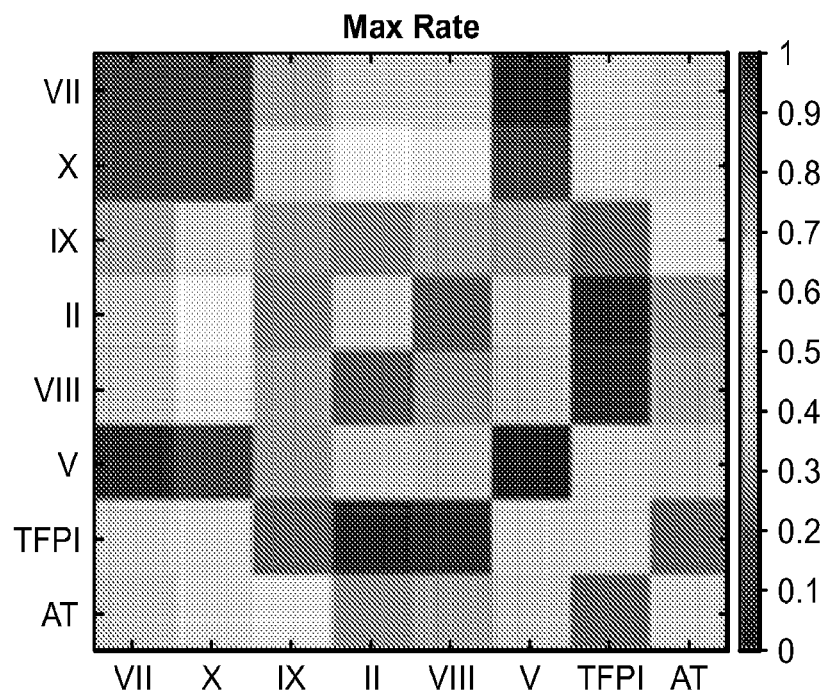

The results of altering AT levels in the 32 control individuals to 40% mean physiologic are presented in FIG. 9B. The scaling is the same as in FIG. 5B and the theoretical population displayed in FIG. 6. As can be seen by visual inspection of FIGS. 6 and 8B, this level of AT deficiency yields individuals with extreme thrombin generation phenotypes with respect to the parameters max level and total thrombin. Comparison with the model representation (FIG. 7) of the same individuals prior to the induction of AT deficiency also shows a systematic increase (~2 fold) in the max rate parameter. None of the nearest neighbors in the theoretical population (FIG. 6) display similar max level and total thrombin parameters. In fact, no individual in the theoretical population displays total thrombin levels of the magnitude characterizing the AT deficient population. The mean total thrombin parameter in the AT deficient group (392776 nM●s) exceeds that of the matching 32 controls (71000 nM●s) by ~5.5 fold.

Single Factor Contribution to Overall Variation in Thrombin Generation

Table 4 presents the results of an analysis testing the sensitivity of model outputs to normal range variation in the 8 initial nonzero factor levels. Each factor was set sequentially to 11 values spanning its normal range, the other 7 factors held at their mean physiologic values and the time courses for all 34 model output species collected. Analysis resulted in the generation of time averaged coefficients of variation for all 34 output species which were manipulated ultimately to rank each factor by the magnitude of the contribution its normal range variation makes to variation in thrombin generation or variation in all model species (see, e.g., FIGS. 12 and 13). It is this ranking, the explained variance, which is presented in Table 4. Panel A: The explained variance is defined as the time averaged coefficient of variation for thrombin for a given factor expressed as a fraction of the sum of all the time averaged coefficients of variation for thrombin for the 8 factors. Panel B: For a given factor, the effect of varying its level across its normal range on all model species is defined as the mean of the time averaged coefficient of variations for all 34 species. The explained variance is then defined as fraction of the sum of the mean time averaged coefficients of variation for the 8 factors.

TABLE 4

| | Panel A | | Panel B | |
|---|---|---|---|---|
| Rank | Factor | IIa Exp Var | Factor | All Factors Exp Var |
| 1 | TFPI | 32.0 | TFPI | 30.9 |
| 2 | II | 16.5 | VIII | 18.2 |
| 3 | VIII | 14.6 | AT | 12.0 |
| 4 | AT | 12.5 | IX | 12.0 |
| 5 | IX | 10.8 | X | 10.7 |
| 6 | X | 5.1 | II | 7.4 |
| 7 | V | 4.3 | V | 5.1 |
| 8 | VII | 4.0 | VII | 3.7 |

These analyses indicate that 2 factors account for ~50% of the observed sensitivity of model output, whether the generation of thrombin is considered or all output species are assessed. Variation in the initial TFPI concentration has the greatest impact on both outputs while variation in the PT level is the second most effective contributor to overall differences in thrombin generation. In general this analysis suggests that TFPI alone or coordinated normal range variation of a few factors may account for the extreme thrombin generation phenotypes in the "normal" hypothetical population.

Factor Pair Induced Variation in Thrombin Parameters

To further explore the relationship between outlying thrombin generation phenotypes and initial factor composition a comparison focusing on the effect of normal range variation of pairs of factors was conducted. The effects of factor pair variation were quantified in terms of the magnitude of the range of potential thrombin parameter values induced by the coordinated variation in the concentrations of each pair of factors. There is shown in FIGS. 10A-D the results of this analysis, with the color scale reflecting the normalized range values. Each thrombin parameter box displays 64 range comparisons as colored squares: 28 factor pair effects are ranked (in duplicate); and the intensity of each single factor (8 total) contribution to variation in the indicated thrombin parameter is represented in the reverse diagonal: bottom right to upper left. Table 5 presents a summary of the most potent factor pair contributors to variation in each thrombin parameter.

TABLE 5

Most potent inducers of alteration in thrombin parameters: single versus factor pair variation.

| Thrombin Parameter | Single Factor | Factor Pair |
|---|---|---|
| Clot Time | TFPI | (TFPI, AT) |
| Max Thrombin | II | (II, AT) > (TFPI, II) |
| Max Rate | AT = TFPI ≥ II | (TFPI, II) = (TFPI, VIII) |
| Total Thrombin | II > AT | (II, AT) |

Normal range variation generates a large distribution of thrombin generation phenotypes. Disparate factor ensembles do yield near identical phenotypes. Normal range variation generates "abnormal phenotypes" i.e. phenotypes characterizing individuals with identified coagulopathies.

Specific factor pairs are identified where coordinate normal range variation in their initial factor concentration yield large changes in thrombin parameters—potential source of extreme phenotypes not representative of normal hemostasis. Such pairs might represent the most likely candidates for monitoring in individuals as predictors of unfortunate events—the emergence in an individual of whatever combination of the two that yields an extreme phenotype.

The concentrations of the components of the coagulation proteome of blood, as measured by standard laboratory tests, vary among apparently healthy individuals, often ranging ±40% to 50% of the mean population value (e.g. Table 1). The significance of this variation remains relatively unexplored in part because the imposition of the category of "healthy" implies these differences are background noise and have no hemostatic consequence.

This study defines the consequences of normal range variation of components of the coagulation proteome by using a mechanism based computational approach that translates coagulation factor concentration data into a representation of an individual's thrombin generation potential. Unique ensembles of the 8 coagulation factors used as initial conditions for the computational modeling were taken to represent individuals in a theoretical healthy population and then compared to normal and "abnormal" individuals, i.e. factor ensembles measured in apparently healthy individuals, actual coagulopathic individuals or artificially constructed factor ensembles representing individuals with specific factor deficiencies. A sensitivity analysis was then performed to rank either individual factors or all possible pairs of factors in terms of their contribution to the overall distribution of thrombin generation phenotypes.

Although limited by its size, the analysis of actual healthy individuals tentatively indicates that the actual normal distribution is constrained to a fraction of the theoretical range of "normal" phenotypes. Comparison of the theoretical population to individuals with a hemorrhagic phenotype shows that normal range variation cannot generate low thrombin generation phenotypes as extreme as those seen in severe hemophilia A or B. Thus the overt hemorrhagic problems seen in affected individuals would not be a predicted outcome of normal range variation. Similarly the extreme high thrombin generation phenotype associated with AT deficiency is not reproduced by normal range variation, potentially suggesting a limit to the severity of the thrombotic risk associated normal range variation. However, such variation does yield some thrombin generation profiles that are "abnormal", i.e. the same as phenotypes characterizing individuals with other less severe composition-based coagulopathies, e.g. that induced by warfarin anticoagulation. Collectively the data suggest that unremarkable composition data from a standard laboratory screen of coagulation factors is not an absolute guarantee of a properly calibrated response to vascular injury. Composition based analyses of larger cohorts of apparently healthy as well as hemostatically challenged individuals, especially those with thrombotic phenotypes, will be necessary to better establish the boundaries of "normal" thrombin generation.

The sensitivity analysis assessing the effect of pairwise variation of coagulation factor concentrations identifies the two inhibitors in the network, TFPI and AT, as potent inducers of overall variation (see Table 2, Table 3). Coordinate expression of extreme high normal range TFPI and AT concentrations is sufficient to yield phenotypes similar to individuals characterized by impaired thrombin generation, i.e. prolonged clot times, and lower max rate, peak and total thrombin values; this effect is amplified when fVIII levels are simultaneously at the low end of their normal range (see Table 3). Identifying factors to which the thrombin output is least sensitive (fVII, fV and fX in this analysis) to their normal range variation, singly or when assessed paired with other factors, could reduce the number of input analytes required to capture the important features of each individual response to injury.

The assessment of the potential of an individual's blood or derived plasma fraction to generate thrombin has and continues to be the primary method of hemostatic monitoring; defects in thrombin generation are identified by relative assay performance differences comparing an individual's outcome to an outcome typical of apparently healthy individuals. Historically these assays are designed to monitor clot time as the indicator of hemostatic competence and are most sensitive to gross differences in composition, e.g. severe deficiencies of specific factors (Rodgers (2004) Diagnostic approach to the bleeding disorder. In: Greer J P, Foerster J, Lukens J N, Rodgers G M, Paraskevas F et al., editors. Wintrobe's Clinical Hematology. Philadelphia: Lippincott Williams & Wilkins. pp. 1511-1528). More recently "global" thrombin assays have provided a more robust account of the flux of thrombin generation in closed systems after tissue factor initiation and their applicability to the diagnosis of coagulopathies is an area of active research (Regnault et al., (2004) Thrombosis research 114: 539-545; Hron et al., (2006) JAMA: 296: 397-402; van Veen et al., (2008) British Journal of Haematology 142: 889-903; Robert et al. (2009) Pharmacological research: The Official Journal of the Italian Pharmacological Society 59: 160-166; Nair et al., (2010) Hemophilia 16 Suppl 5: 85-92; Castoldi et al., (2011) Thrombosis Research 127 Suppl 3: S21-25)

However, as with the clot based assays, those readouts, whether defined as typical or atypical, do not explain the origins of their features and as to why one individual appears the same or different from another. This modeling based approach requires coagulation factor analyses of each individual's citrate plasma sample, but yields a representation of an individual's coagulation state that is easy to dissect, based on current understanding of the dynamics reflecting proteins at their physiologic concentrations and native conformations. It creates a mechanism-based rationale for asking the question as to whether individuals can be relatively closer to a hemorrhagic or thrombotic problem and how composition changes in a subset factors driven by other disease processes, e.g. inflammatory syndromes, might have different hemostatic consequences in different individuals.

Although a preferred embodiment of the invention has been described using specific terms, such description is for illustrative purposes only, and it is to be understood that changes and variations may be made without departing from the spirit or scope of the following claims.

Figure 15:
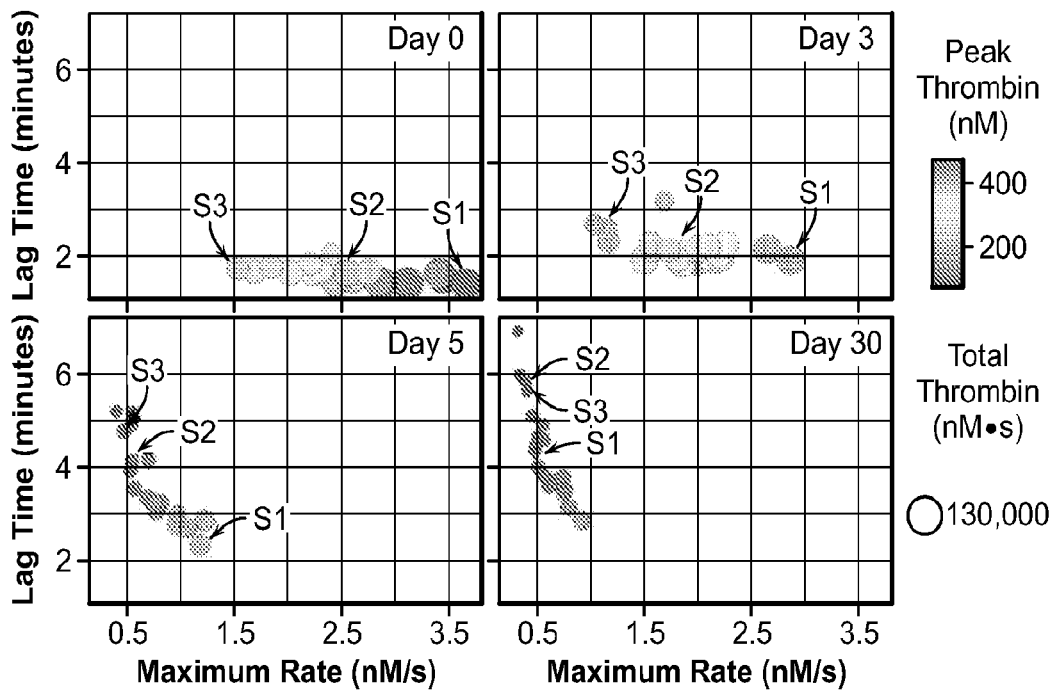
FIG. 15 provides a set of graphs each presenting four coagulation variables for a set of subjects at various time points showing the kinetics of warfarin anticoagulation in patients with atrial fibrillation. Each graph represents a "screen shot" of the dynamic visualization method of the invention. Thrombin generating capacity was simulated by inputting each subjects' factor composition into our mathematical model. Each point (circle) in the figure is representative of a single individual's thrombin generating capacity before and during warfarin anticoagulation. All subjects, including the 3 highlighted (S1, S2 and S3), show a time dependent reduction in thrombin generating capacity (marginally increased lag time, decreased maximal rate, decreased peak and total thrombin) in response to warfarin therapy. Note that the peak thrombin scale ranges from 0-500 nM.

Example 2: Simulated Thrombin Generation During Warfarin Anticoagulation in Atrial Fibrillation Patients with atrial fibrillation were enrolled and provided plasma samples just prior to commencing warfarin therapy (day 0) and on days 3, 5, 7, 14 and 30 of warfarin therapy. The factor composition for each unique plasma sample was used to simulate the time course of thrombin generation using two empirically validated mathematical models termed the "Base model" and the "Protein C model". The mechanism of warfarin anticoagulation is well-established (Hirsh, J. et al., Chest 114, 445S-469S (1998)) and the data presented in FIG. 15, depicting thrombin generation parameters derived from the "Base model" are consistent with previous reports (Hirsh, J. et al., Chest 114, 445S-469S (1998)). FIG. 15 shows that all subjects, including the 3 highlighted (S1, S2 and S3), have a reduced thrombin generating capacity in response to warfarin therapy. After 3 days on warfarin, subject S1, S2 and S3 have reduced peak and total thrombin and a reduced maximal rate of thrombin generation compared to baseline. In addition, each subject has a slightly prolonged lag time. This trend continues through day 5 where S2 and S3 are approaching a stable thrombin generating capacity suggesting stable anticoagulation. By day 30, all 3 subjects are stably anticoagulated which is implied by their consistent but drastically reduced thrombin generating capacity.

Figure 16:
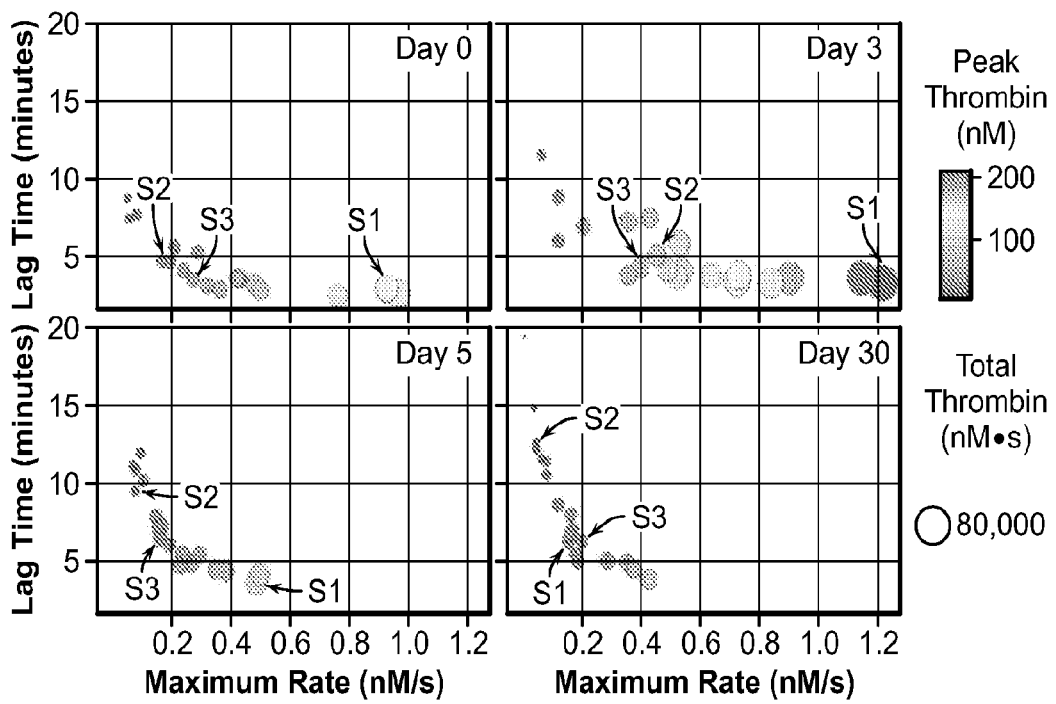
FIG. 16 provides a set of graphs each presenting four coagulation variables for a set of subjects at various time points showing the effect of the protein C pathway on the kinetics of Warfarin anticoagulation in patients with atrial fibrillation. Each graph represents a "screen shot" of the dynamic visualization method of the invention. Thrombin generating capacity was simulated by inputting each subjects' factor composition into our mathematical model containing the protein C pathway. Each point (circle) in the figure is representative of a single individual's thrombin generating capacity before and during warfarin anticoagulation. All subjects show a time dependent reduction in thrombin generating capacity (increased lag time, increased maximal rate, decreased peak and total thrombin) in response to warfarin therapy. Most subjects, including the subjects highlighted (S1, S2 and S3), have an increased maximal rate, peak and total thrombin and a marginally increased lag time 3 days after starting warfarin therapy. After day 3, every subjects' thrombin generating capacity decreases in a similar fashion to that shown using our "Base model" (FIG. 15). Note that the peak thrombin scale ranges from 0-200 nM. Note differences in individuals and indicator of risk potential.

Using a similar approach to that employed in the creation of FIG. 15, thrombin generation data displayed in FIG. 16 was generated based on a mathematical simulation that incorporated the effect of the protein C pathway whereas the previous model did not. As with the Base model, all subjects, including those highlighted (S1, S2 and S3; same as highlighted in FIG. 15) become stably anticoagulated as a result of warfarin therapy. The key difference occurs after 3 days on warfarin: most subjects including S1, S2 and S3 paradoxically have an increased thrombin generating capacity compared to baseline. The simulations suggest that peak and total thrombin and the maximal rate of thrombin generation increases during the initial phase of warfarin therapy. After 3 days on warfarin, the lag time remains constant for all three highlighted subjects as it does for >75% of the other subjects. After 5 days on warfarin all 3 highlighted subjects have a reduced thrombin generating capacity and subject S2 and S3 become stably anticoagulated. By day 30 all 3 subjects are stably anticoagulated.

Use of the method shows that the atrial fibrillation group is stably anticoagulated within 5 days of commencing warfarin therapy. These data are consistent with the well-established role of warfarin in decreasing the production of vitamin K dependent proteins (Hirsh, J. et al., Chest 114, 445S-469S (1998)) which results in reduced thrombin generation in vivo (Conway, E. M. et al., J. Clin. Invest. 80, 1535-1544 (1987)), in vitro (Dargaud, Y. et al., J. Thromb. Haemost. 6, 962-968 (2008)) and in silico (Orfeo, T. et al., PLoS. One. 6, e27852 (2011)). Adding the protein C pathway to the mathematical model of the invention and plotting the data using dynamic visualization, identified a theoretical window in which patients on warfarin may be at an increased risk of thrombosis. The claimed method showed that all subjects have an increased thrombin generating capacity 3 days after starting warfarin therapy. After day 3, the thrombin generating capacity decreases substantially as each subject becomes stably anticoagulated. This paradoxical and theoretical increase in thrombotic risk can be explained by the relatively short half-life of protein C compared to other vitamin K dependent proteins such as prothrombin and fX (Brummel-Ziedins, K. et al., Blood coagulation and fibrinolysis in Wintrobe's Clinical Hematology (ed. Greer, J.) 677-774 (Lippincott Williams & Wilkins, Philadelphia, 2003)). Since protein C levels decrease faster during warfarin therapy than prothrombin and fX, there is a window of time where the anticoagulant pathway afforded by protein C is diminished to a greater extent than that of procoagulant pathways comprising the other vitamin K dependent proteins. Interestingly, an increased thrombin generating capacity on day 3 is only marginally associated with an increased lag time. The lag time is the thrombin parameter which most closely resembles the clot time in the PT assay which is clinically used to monitor warfarin anticoagulation. The simulated lag times are consistent with the insensitivity of the PT assay to protein C levels (Khor, B. & Van Cott, E. M., Am J Hematol. 85, 440-442 (2010)) but nonetheless show a theoretical increase in thrombin generating capacity during the early stages of warfarin anticoagulation. Therefore, modeling the kinetics of warfarin anticoagulation may be useful in identifying individuals who are most at risk of thrombosis during the early stages of warfarin anticoagulation.

Figure 17:
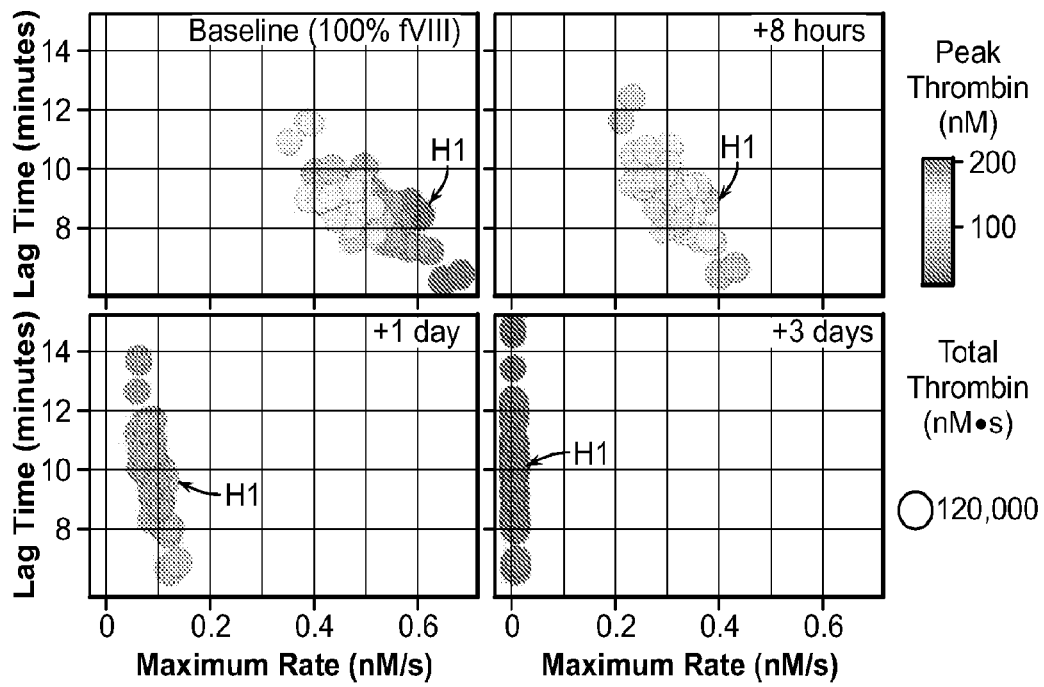
FIG. 17 provides a set of graphs each presenting four coagulation variables for a set of subjects at various time points showing the dynamic reduction of thrombin generation parameters over time in a severe haemophilia A population receiving factor VIII replacement. Each graph represents a "screen shot" of the dynamic visualization method of the invention. Thrombin generating capacity was simulated by inputting each subjects' factor composition into our mathematical model. Each point (circle) in the figure is representative of a single individual's thrombin generating capacity. Since each subject has clinically severe haemophilia A (fVIII<1%), the fVIII concentration was set at 100% at time zero (baseline). The thrombin generating capacity was followed over 7 half-lives of fVIII ($t_{1/2}$=12.2 hours) which represents the approximate time between prophylactic fVIII doses. All individuals, including subject H1, showed a decrease in thrombin generating capacity (decreased maximal rate and peak thrombin and marginally decreased total thrombin and marginally increased lag time) as fVIII decayed. Note that the peak thrombin scale ranges from 0-200 nM.

Example 3: Simulated Thrombin Generation During fVIII Prophylaxis in Haemophilia A Patients with severe haemophilia were enrolled and provided plasma samples which were used to determine their factor composition. The factor composition for each unique plasma sample was used to simulate the time course of thrombin generation using the empirically validated "Base model". Since all subjects have clinically severe haemophilia A (fVIII<1%) and their fVIII levels varied significantly at the time of blood collection, the fVIII concentration was set at 100% at time zero (baseline) to reflect the ideal goal of the administered fVIII dose. The thrombin generating capacity was followed over 7 half-lives of fVIII ($t_{1/2}$=12.2 hours) to demonstrate the theoretical fluctuations in thrombin generating capacity during the course of fVIII prophylaxis. At 100% ("baseline") fVIII, there is significant individual variation in thrombin generating capacity among individuals with severe haemophilia A (FIG. 17) which is consistent with previous work (Dargaud, Y. et al., *Thromb. Haemost.* 93, 475-480 (2005)). The maximum rate of thrombin generation ranges from 0.35 to 0.7 nM/s, peak thrombin ranges from 100 to 200 nM and lag time ranges from 7 to 12 minutes. Using subject H1 as an example, it is evident that maximal rate of thrombin generation and peak thrombin levels decrease as fVIII decays. The lag time and total thrombin levels are affected less in this tissue factor stimulated model of coagulation and thrombin generation.

Figure 18:
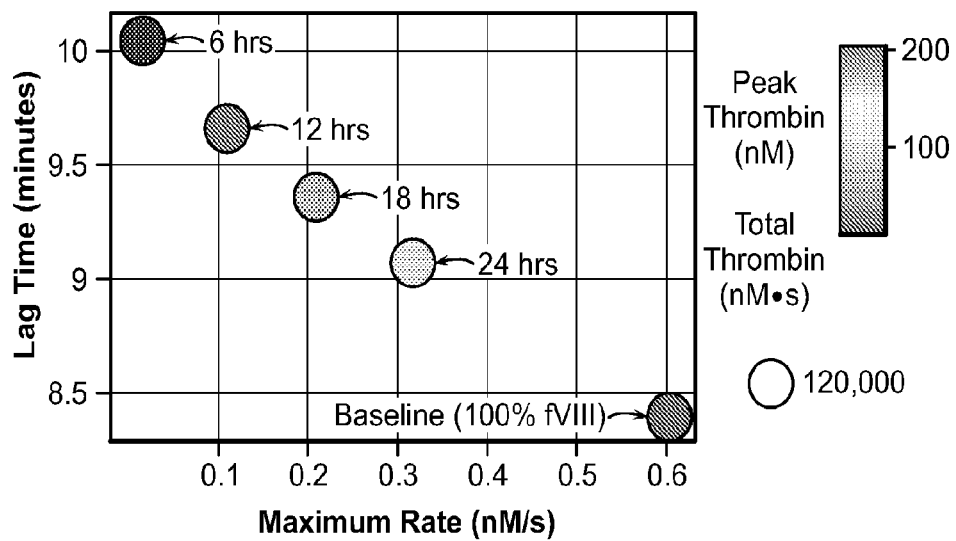
FIG. 18 is a graph showing the effect of factor VIII product half-life on the dynamics of thrombin generation over time 32 hours post administration of fVIII. Thrombin generating capacity was simulated by inputting subject H1's factor levels into our mathematical model. The thrombin generation capacity is also shown at 32 hours for 4 hypothetical fVIII products with half-lives of 6, 12, 18 and 24 hours. The baseline (100% fVIII) thrombin generating capacity at time zero is shown as a reference. By 32 hours, the 6 hour product has decayed to ~1% which coincides with the approximate timing between prophylactic doses of fVIII. Note that the peak thrombin scale ranges from 0-200 nM.

To show the effect of increased fVIII product half-life on thrombin generating capacity, thrombin parameters were generated using our "Base model" and the factor levels of subject H1 over 7 half-lives of fVIII. The effect of 4 hypothetical fVIII products on thrombin generation is shown in FIG. 18. The products' have half-lives range from 6 (6 hrs) to 24 hours (24 hrs). FIG. 18 depicts baseline thrombin generating capacity just after fVIII infusion (i.e. 100% fVIII) for subject H1 and the thrombin generating capacity expected after 32 hours with the 4 hypothetical fVIII products. The 32 hour time point represents the time required for the 6 hour product to fall to 1% which, based on modern prophylactic regiments, is when an additional dose of (6 hour) fVIII would be required (Manco-Johnson, M., *Haemophilia*. 13 Suppl 2, 4-9 (2007)). By definition the 12, 18 and 24 hour fVIII products have not decayed as quickly and therefore do not need to be supplemented with an additional dose of fVIII at this time. When visualized over time, once a given fVIII product level falls below 1%, the plot disappears. The time to disappearance for each fVIII product represents the approximate relative time between fVIII doses.

In monitoring thrombin generating capacity among patients with severe haemophilia, dynamic visualization of the data shows that the maximal rate of thrombin generation and peak thrombin decreases dramatically as fVIII decays while the lag time and total thrombin are only marginally decreased. As reviewed previously (Manco-Johnson, M., *Haemophilia*. 13 Suppl 2, 4-9 (2007)), the goal in prophylactic factor replacement therapy is to keep the fVIII concentration above 1% to significantly reduce the risk of bleeding. The data shows the relative timing of reduced thrombin generating capacity in haemophilia A during prophylactic fVIII replacement therapy and illustrates very clearly the clinical benefit of fVIII products with a prolonged half-life.

Example 4: Empirical Thrombin Generation During Pregnancy

Figure 19:
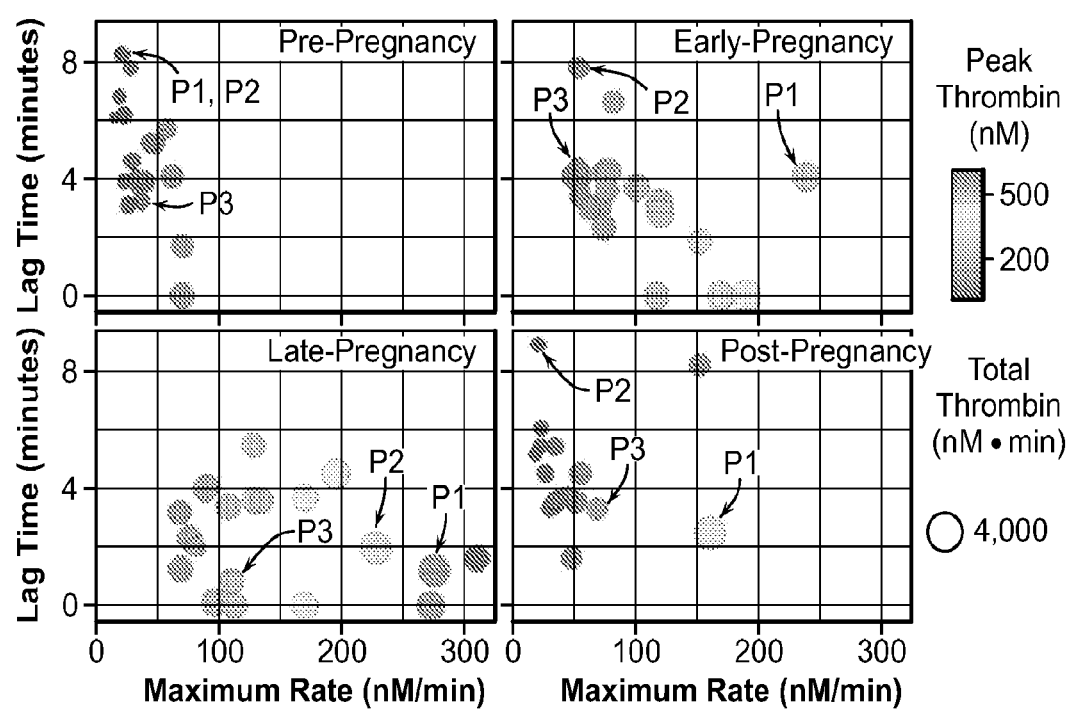
FIG. 19 provides a set of graphs each presenting four coagulation variables for a set of subjects at various time points showing the dynamics of thrombin generation during the course of pregnancy. Each graph represents a "screen shot" of the dynamic visualization method of the invention. Thrombin generating capacity was determined empirically using a thrombin generation assay. Each point (circle) in the figure is representative of a single individual's thrombin generating capacity. All subjects, including the 3 highlighted (P1, P2 and P3), have increased thrombin generating capacity (decreased lag time, increased maximal rate, increased peak and total thrombin) in early pregnancy. The thrombin generation capacity increases further in late pregnancy and post-pregnancy returns to near baseline levels for most individuals. Note that the peak thrombin scale ranges from 0-750 nM.

Patients planning pregnancy were enrolled and provided plasma samples which were used to empirically measure thrombin generation using a thrombin generation assay. FIG. 19 shows that most subjects (16 of 19) have a lag time of between 3 and 8 minutes at baseline (pre-pregnancy). All subjects have a maximum rate of thrombin generation less than 100 nM/min and peak thrombin less than 200 nM. Total thrombin ranges from 745 nM-min to 2675 nM-min in these individuals at baseline. In early pregnancy (11 to 15 weeks), there is a trend toward a procoagulant state with the lag time decreasing, maximum rate of thrombin generation increasing and both peak and total thrombin increasing. In late pregnancy (30 to 34 weeks), there is a further reduction in the lag time. The maximum rate of thrombin generation and peak and total thrombin levels increase further compared to early pregnancy. After pregnancy and after breast feeding has ceased (6 to 24 months after delivery), the thrombin generating capacity returns to the range observed pre-pregnancy. Post-pregnancy, the lag time is between 3 and 8 minutes for most individuals and the maximum rate of thrombin generation is less than 100 nM/min for all but 2 individuals. Peak and total thrombin are also similar to pre-pregnancy values in all but 2 individuals.

Analysis of the pregnant population shows that the utility of this method of data presentation is not exclusive to simulated thrombin generation parameters but can also be used to chart thrombin generating capacity using empirical parameters from thrombin generation assays. Consistent with previous reports (Eichinger, S. et al., *Thromb Haemost* 82, 1232-1236 (1999); (Dargaud, Y. et al., *Thromb Haemost* 103, 469-471 (2010); and Rosenkranz, A. et al., *Thromb Haemost* 99, 331-337 (2008)), the pregnant population has an increased procoagulant tendency in early pregnancy which increases further in late pregnancy. After delivery and cessation of breast feeding dynamic visualization of the data shows that thrombin generating capacity returns to pre-pregnancy levels. The plot also very clearly identifies subjects who contain an endogenous activator within their plasma (lag time=0 minutes). Using a previously described assay (Butenas, S. et al., *Thromb. Haemost.* 99, 142-149 (2008)), it was determined that these subjects had endogenous fIXa or fXIa activity (Wulfkuhle, K. C. et al., *J Thromb Haemost* 9 Suppl 2, 431 (2011)).

The marriage between simulated thrombin generation and the dynamic visualization method allows for rapid identification of individuals with abnormal thrombin generation kinetics. In recent years, considerable effort and resources have been devoted to the development of personalized medicine, but many hurdles remain (*Nat. Biotechnol.* 30, 1 (2012)). Any tool which simplifies the identification of at risk individuals will likely streamline the implementation of personalized therapies, thus improving patient care and outcomes. The ways that the general population and scientific community consume and uses data have changed drastically over the past few years. As recently as 5 years ago the utility of the dynamic visualization method would have been limited to a desktop computer. Today, however, the ubiquity of the internet combined with advances in computing power make this method accessible via desktop computers as well as netbooks and smartphones.

Examples 2-4 were carried out using the following materials and methods.

Simulated Thrombin Generation

For each unique plasma sample, the time course of thrombin generation was simulated using two empirically validated mathematical models termed the "Base model" (Hockin, M. F. et al., *J Biol Chem* 277, 18322-18333 (2002)); & (Butenas, S. et al., *J. Biol. Chem.* 279, 22875-22882 (2004)) and the "Protein C model" (Bravo, M. C. et al., *BMC. Syst. Biol* 6, 45 (2012)). In principle, the models differ in their ability to represent the anticoagulant properties of the vasculature. In this regard, the "Base model" describes extravascular coagulation whereas the "Protein C model" describes the coagulation response in the context of the inhibitory potential derived from the vascular endothelium. Both models are built around a series of ordinary differential equations which make use of rate constants derived from experimental measurements made under conditions of saturating concentrations of phospholipids (Hockin, M. F et al., *J Biol Chem* 277, 18322-18333 (2002)). The "Base model" makes use of the following inputs: empirically determined active concentrations of fII, fV, fVII/fVIIa, fVIII, fix, fX and the anticoagulants tissue factor pathway inhibitor (TFPI) and antithrombin (AT). The "Protein C model" uses all inputs from the "Base model" as well as the empirically determined active protein C concentration and nominal concentrations of thrombomodulin (TM), an essential anticoagulant cofactor found on the vascular endothelium, which can be altered to represent the amount of TM found in various vessels. For both models, the starting concentration of fVIIa was set to 1% of the starting fVII concentration. The models are initiated by exposing the inputs to 0.5 pM tissue factor for haemophilia simulations (Base model only) or 5 pM tissue factor for warfarin anticoagulation simulations (Base and Protein C models). Using this approach, the concentration versus time profiles for all reactants, including thrombin are determined. Thrombin generation parameters such as the lag time (time to 2 nM thrombin), the maximum rate of thrombin generation (max rate), peak thrombin and total thrombin (area under the thrombin generation profile) can be determined from the time course of thrombin generation (Brummel-Ziedins, K. et al., *J. Thromb. Haemost.* 3, 1472-1481 (2005)).

Empirical Thrombin Generation

Thrombin generation assays were performed as previously described (McLean, K. C. et al., *Am J Obstet Gynecol* In Press, DOI: 10.1016/j.ajog.2012.05.027 (2012); & Hemker, H. C. et al., *Pathophysiol. Haemost. Thromb.* 32, 249-253 (2002)). Briefly, a 20 μL solution containing 2.5 mM of the thrombin substrate, Z-GGR-AMC and 0.1 M $CaCl_2$ was incubated with 80 μL of citrated plasma containing 0.1 mg/mL corn trypsin inhibitor for 3 minutes at 37° C. After this incubation period, thrombin generation was initiated by the addition of 20 μL of relipidated TF (5 pM final) and PCPS (20 μM final) in HEPES buffered saline. As thrombin cleaves Z-GGR-AMC there is an increase in fluorescence which can be used with a series if thrombin standards to calculate the amount of thrombin formed over time in plasma. Using this experimental system, thrombin generation was monitored continuously using a plate reader (SYNERGY4, BioTek, Winooski, Vt., USA). Thrombin generation parameters such as the lag phase, the max rate, peak thrombin and total thrombin can be determined from the empirically generated thrombin generation plot.

Atrial Fibrillation Population

Patients with diagnosed atrial fibrillation (detailed patient characteristics can be found in Table 6; n=20; 10 male and 10 female aged 59±6.25 years) were recruited and enrolled by Dr. A Undas and advised according to a protocol approved by the Jagiellonian University Ethical Committee (Krakow, Poland). Informed written consent was obtained from all the individuals. Patients varied substantially with respect to their individual risk factors for stroke. Blood was collected from the enrolled patients on 6 occasions during the study period and used to make citrated platelet poor plasma which was aliquoted and stored at −80° C. The first sample was collected just prior to starting warfarin anticoagulation. Subsequent samples were collected on days 3, 5, 7, 14 and 30 after initiating warfarin therapy. On each day, each subjects' plasma composition was determined (6 days× 20 subjects=120 unique plasma compositions) primarily by using routine activity-based clinical clotting assays (Brummel-Ziedins, K. et al., *J. Thromb. Haemost.* 6, 104-110 (2008)). The concentrations of factors II, V, VII/VIIa, VIII, IX, X and the anticoagulants TFPI and AT were used to simulate thrombin generation using the "Base model" and "Protein C model".

TABLE 6

Atrial fibrillation patient characteristics.

| Patient | Sex | Age | CAD | HT | DB | SM | HC | ST | ASA | ACEI | STAT | HF | BMI |
|---|---|---|---|---|---|---|---|---|---|---|---|---|---|
| 1 | M | 68 | 0 | 1 | 1 | 0 | 1 | 1 | 1 | 1 | 1 | 1 | 35 |
| 2 | F | 59 | 0 | 0 | 0 | 0 | 0 | 0 | 0 | 0 | 0 | 0 | 21 |
| 3 | M | 66 | 0 | 1 | 0 | 1 | 1 | 0 | 0 | 1 | 1 | 0 | 27 |
| 4 | F | 58 | 1 | 0 | 1 | 0 | 0 | 1 | 1 | 0 | 0 | 1 | 34 |
| 5 | M | 59 | 0 | 1 | 0 | 1 | 1 | 0 | 0 | 1 | 1 | 1 | 28 |
| 6 | F | 54 | 0 | 1 | 0 | 0 | 0 | 0 | 0 | 1 | 0 | 0 | 28 |
| 7 | F | 52 | 0 | 1 | 0 | 1 | 0 | 0 | 0 | 1 | 0 | 0 | 29 |
| 8 | F | 60 | 0 | 0 | 0 | 0 | 0 | 0 | 0 | 0 | 0 | 0 | 21 |
| 9 | F | 63 | 0 | 1 | 1 | 0 | 1 | 0 | 0 | 1 | 1 | 1 | 28 |
| 10 | M | 68 | 0 | 1 | 0 | 0 | 0 | 0 | 0 | 1 | 0 | 0 | 29 |
| 11 | F | 59 | 0 | 1 | 0 | 0 | 1 | 0 | 0 | 1 | 1 | 0 | 24 |
| 12 | F | 51 | 0 | 1 | 0 | 0 | 1 | 0 | 0 | 1 | 1 | 0 | 34 |
| 13 | M | 48 | 0 | 1 | 0 | 0 | 1 | 0 | 0 | 1 | 1 | 0 | 31 |
| 14 | M | 69 | 0 | 1 | 0 | 1 | 0 | 0 | 0 | 1 | 0 | 0 | 31 |
| 15 | M | 51 | 1 | 0 | 0 | 1 | 0 | 0 | 1 | 0 | 0 | 0 | 28 |
| 16 | M | 59 | 0 | 1 | 0 | 0 | 1 | 0 | 0 | 1 | 1 | 0 | 24 |
| 17 | F | 53 | 0 | 1 | 0 | 0 | 1 | 0 | 0 | 1 | 1 | 1 | 30 |
| 18 | M | 61 | 0 | 0 | 0 | 0 | 0 | 0 | 0 | 0 | 0 | 0 | 27 |
| 19 | M | 64 | 0 | 0 | 0 | 0 | 1 | 0 | 0 | 0 | 1 | 1 | 25 |
| 20 | F | 54 | 1 | 1 | 0 | 1 | 1 | 1 | 1 | 0 | 1 | 1 | 31 |

Yes = 1;
No = 0;
CAD: Coronary artery disease;
HT: Hypertension;
DB: Diabetes;
SM: Smoker;
HC: Hypercholesteremia
ST: Stroke/transient ischemic attack
ASA: Aspirin;
ACEI: ACE inhibitors
STAT: Statins;
HF: Heart failure
BMI: Body mass index Haemophilia Population Patients with clinically severe haemophilia A (fVIII: C<1% at the time of diagnosis, age range 16-33) were recruited and enrolled by Dr. G-E Rivard and advised according to a protocol approved by the Institutional Review Boards at the Centre Hospitalier Universitaire Sainte-Justine (Montreal, QC) and by the University of Vermont Committees on Human Research (Burlington, Vt.) (Gissel, M. et al., *Haemophilia.* 18, 193-199 (2012)). Informed written consent was obtained from all individuals. Each subjects' plasma composition was determined primarily by using routine activity-based clinical clotting assays. The concentrations of fII, fV, fVII/fVIIa, fVIII, fIX, IX and the anticoagulants TFPI and AT were used as measured to simulate thrombin generation using the "Base model". Since all subjects have clinically severe haemophilia A (fVIII<1%) and their fVIII levels varied significantly at the time of blood collection, the fVIII concentration was electronically set at 100% at time zero (baseline). The thrombin generating capacity was followed over 7 half-lives (6-24 hours) of fVIII to demonstrate the theoretical fluctuations in thrombin generating capacity during the course of fVIII prophylaxis.

Pregnant Population

Women who intended conception were enrolled in the initial study (Hale, S. A. et al., *Reprod. Sci* 16, 1091-1096 (2009)). Study participants (aged 18-40 years) were healthy non-smokers with no history of hypertension, diabetes mellitus, autoimmune disease or haemostatic disorders. At the time of enrollment, all women had regular menstrual cycles (n=20 pregnant; n=10 non-pregnant controls). Blood was collected from enrolled patients up to 4 times during the study. Blood was centrifuged immediately to produce citrated platelet poor plasma which was subsequently aliquoted and stored at −80° C. Pre-pregnancy samples were collected during the follicular phase of the menstrual cycle. Early and late pregnancy samples were collected at 11-15 menstrual weeks and 30-34 weeks, respectively. Post-pregnancy samples were collected after breastfeeding ceased which was between 6 and 24 months after delivery in all cases. Post-pregnancy samples were also collected in the follicular phase of the menstrual cycle. Enrolled women who did not become pregnant remained in the study as control subjects (data not shown). These women provided blood samples pre-pregnancy and approximately 2.5 years after the initial blood draw. The thrombin generation capacities of these women were previously reported (McLean, K. C. et al., *Am J Obstet Gynecol* In Press, DOI: 10.1016/j.ajog.2012.05.027 (2012)). The research protocols were approved by the University of Vermont Committees on Human Research. All women provided written informed consent.

Dynamic Visualization of Thrombin Generation

Thrombin generation parameters were determined either computationally or empirically as described in the "*Simulated/Empirical thrombin generation*" sections of the *Online Methods*. Thrombin parameters depicting the kinetics of warfarin anticoagulation or the net result of decreasing fVIII during prophylaxis in haemophilia A were generated using the computational models. Thrombin parameters depicting global haemostatic changes during pregnancy were determined empirically. For each individual, the lag time (time to 2 nM thrombin), maximal rate of thrombin generation, peak thrombin and total thrombin (area under the curve) were plotted against time using the motion chart gadget which is available in Google Docs (Mountain View, Calif.) spreadsheets. Using this gadget, 5 dimensional plots were created. In these plots, the time to lag time is depicted on the y-axis, maximal rate of thrombin generation is depicted on the x-axis, peak thrombin is represented by the colour, and total thrombin is represented by the relative size of each data point. A large, red circle in the lower right quadrant is representative of a high thrombin generating capacity whereas a small, blue circle in the upper left quadrant represents a low thrombin generating capacity. The time component is shown by animating each point to move as thrombin generation parameters change over time. Videos depicting changes in thrombin generation over time were captured using TechSmith® Camtasia Recorder 8 software (Okemos, Mich.). Each figure was created by taking screen captures of relevant videos.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to subject matter present in U.S. Provisional Application No. 61/631,286, incorporated herein by reference. All patents and publications mentioned in this specification are herein incorporated by reference to the same extent as if each independent patent and publication was specifically and individually indicated to be incorporated by reference.

What is claimed is:

1. A method for assessing a subject's ability to generate thrombin, the method comprising the steps of:

(a) obtaining a thrombin generation profile of the subject from measurements of the concentrations of factors II, V, VII/VIIa, VIII, IX, and X, tissue factor pathway inhibitor (TFPI), protein C (PC), and antithrombin (AT) in a biological sample from the subject; and (b) displaying the thrombin generation profile in a visual form, wherein the thrombin generation profile comprises the parameters: maximum level of thrombin generation, maximum rate of thrombin generation, total thrombin generated, and clot time;

wherein the measurements of factors II, V, VII/VIIa, VIII, IX, and X, TFPI, PC, and AT are used to derive said parameters for the thrombin generation profile, wherein a thrombin generation profile comprising a greater than 3-fold decrease in clot time and greater than 3-fold increase in maximum level of thrombin generation, maximum rate of thrombin generation, and total thrombin generated, relative to a respective reference for each of said parameters comprising the thrombin generation profile, indicates a propensity of the subject for blood clotting; and wherein a thrombin generation profile comprising a greater than 3-fold increase in clot time and a greater than 3-fold decrease in maximum level of thrombin generation, maximum rate of thrombin generation, and total thrombin generated, relative to the respective reference for each of said parameters comprising the thrombin generation profile, indicates a propensity of the subject for bleeding.

2. The method of claim 1, wherein the thrombin generation profile is displayed on a display device.

3. The method of claim 2, wherein the display device is a hand held computer, smart phone, cellular telephone, tablet computer, or personal digital assistant.

4. The method of claim 1, wherein the parameters are clinically or computationally derived.

5. The method of claim 1, further comprising the use of one or more measurements of biomarker levels or activity, wherein the biomarker is selected from the group consisting of activated partial thromboplastin time, blood pressure, body mass index, results of clot-based assays, clot elasticity, D-dimer and fibrin degradation product levels, euglobulin clot lysis, estrogen levels, factor V Leiden, fibrin, fibrinolysis, fibrinogen activity, genetic mutations, high density lipoprotein levels, low density lipoprotein levels, patient age, plasma composition, platelet count, platelet function, red blood cells, protein S, plasminogen, prothrombin time, prothrombin ratio, results of a thrombin generation assay, smoking status, and results obtained from a calibrated automated thrombogram, thrombogram, or thromboelastography.

6. The method of claim 1, further comprising the use of patient data relating to bleeding score, drug dosages, drug metabolite levels, HIV status, inflammatory state, pregnancy or post-pregnancy status, and trauma.

7. The method of claim 1, wherein the subject is identified as having hemophilia A, B, C, or von Willebrand's disease.

8. A non-transitory computer readable medium containing program instructions executable by a processor, the computer readable medium comprising:
    program instructions for generating a thrombin generation profile of a subject from measurements of the concentrations of factors II, V, VII/VIIa, VIII, IX, and X, tissue factor pathway inhibitor (TFPI), protein C (PC), and antithrombin (AT) in a biological sample from the subject;
    program instructions for obtaining the parameters: maximum level of thrombin generation, maximum rate of thrombin generation, total thrombin generated, and clot time, the parameters are derived from the measurements of factors II, V, VII/VIIa, VIII, IX, and X, TFPI, PC, and AT; and
    program instructions for determining the propensity of the patient for blood clotting and bleeding, the determination is based on the parameters; and
    program instructions for displaying the thrombin generation profile in a visual form;
    wherein a thrombin generation profile comprising a greater than 3-fold decrease in clot time and greater than 3-fold increase in maximum level of thrombin generation, maximum rate of thrombin generation, and total thrombin generated, relative to a respective reference for each of said parameters comprising the thrombin generation profile, indicates a propensity of the subject for blood clotting; and
    wherein a thrombin generation profile comprising a greater than 3-fold increase in clot time and a greater than 3-fold decrease in maximum level of thrombin generation, maximum rate of thrombin generation, and total thrombin generated, relative to the respective reference for each of said parameters comprising the thrombin generation profile, indicates a propensity of the subject for bleeding.

9. The non-transitory computer readable medium of claim 8, wherein the inputting one or more measurements of biomarker levels or activity, wherein the biomarker is selected from the group consisting of activated partial thromboplastin time, blood pressure, body mass index, results of clot-based assays, clot elasticity, D-dimer and fibrin degradation product levels, CRP levels, euglobulin clot lysis, estrogen levels, fibrin, fibrinolysis, fibrinogen activity, genetic mutations, high density lipoprotein levels, light density lipoprotein levels, factor V Leiden, IL-6 levels, patient age, plasma composition, platelet count, platelet function, progesterone levels, red blood cells, protein S, plasminogen, prothrombin time, prothrombin ratio, results of a thrombin generation assay, and results obtained from a calibrated automated thrombogram, thrombogram, or thromboelastography.

* * * * *